(12) United States Patent
Tao et al.

(10) Patent No.: US 9,075,056 B2
(45) Date of Patent: Jul. 7, 2015

(54) REAGENTS AND METHODS FOR PHOSPHORYLATION/DEPHOSPHORYLATION ANALYSES

(75) Inventors: Weiguo Andy Tao, West Lafayette, IN (US); Anton B. Iliuk, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 188 days.

(21) Appl. No.: 13/641,038

(22) PCT Filed: Apr. 13, 2011

(86) PCT No.: PCT/US2011/032331
§ 371 (c)(1),
(2), (4) Date: Dec. 28, 2012

(87) PCT Pub. No.: WO2011/130416
PCT Pub. Date: Oct. 20, 2011

(65) Prior Publication Data
US 2013/0095502 A1    Apr. 18, 2013

Related U.S. Application Data

(60) Provisional application No. 61/323,442, filed on Apr. 13, 2010, provisional application No. 61/416,714, filed on Nov. 23, 2010.

(51) Int. Cl.
| | | |
|---|---|---|
| *G01N 33/573* | (2006.01) | |
| *G01N 33/53* | (2006.01) | |
| *C08G 73/02* | (2006.01) | |
| *C08G 65/338* | (2006.01) | |
| *G01N 33/58* | (2006.01) | |
| *B82Y 15/00* | (2011.01) | |

(52) U.S. Cl.
CPC ............ *G01N 33/573* (2013.01); *C08G 73/028* (2013.01); *C08G 65/338* (2013.01); *Y10S 977/70* (2013.01); *Y10S 977/92* (2013.01); *B82Y 15/00* (2013.01); *G01N 33/587* (2013.01); *G01N 33/58* (2013.01); *G01N 2440/14* (2013.01)

(58) Field of Classification Search
CPC ...... G01N 33/573; G01N 33/53; G01N 33/50; G01N 33/48; G01N 33/00; C08G 73/028; C08G 73/00; C08G 65/338; C08G 65/32; C08G 73/02; C08G 65/30; C08G 65/00
USPC .......... 436/103; 435/7.4, 7.1, 7.92, 7.94, 188, 435/183; 422/430, 50
See application file for complete search history.

(56) References Cited

U.S. PATENT DOCUMENTS

| | | |
|---|---|---|
| 2006/0121544 A1 | 6/2006 | Boge et al. |
| 2008/0261321 A1 | 10/2008 | Patton et al. |
| 2009/0023144 A1 | 1/2009 | Sun |
| 2010/0009381 A1 | 1/2010 | Agnew et al. |
| 2010/0087008 A1 | 4/2010 | Tao |

OTHER PUBLICATIONS

International Search Report and Written Opinion Issued by the Korean Intellectual Property Office, dated Dec. 19, 2011, for related International Application No. PCT/2011/032331; 14 pages.

*Primary Examiner* — Christine T Mui
(74) *Attorney, Agent, or Firm* — Brown Rudnick LLP; Adam M. Schoen

(57) ABSTRACT

Disclosed herein are reagents that include a moiety that includes a metal such as titanium and that readily binds to phosphorylated molecules the reagents also include at least one moiety that produces a signal or that binds to a molecule that produces a signal. The reagent may also include a moiety that binds to a larger molecule or to a surface. Some forms of the reagent include a dendrimer that can simultaneously bind to multiple metal moieties that include a metal such as titanium and multiple moieties that can be used to detected bound molecules. These reagents can be used in detection and/or measurement and/or at least partial purification of phosphorylated molecules. These reagents and methods using them are used to analyze proteins, polypeptides, nucleic acids, phospholipids and the like. They are readily adapted for use in gels, blots, plate based high through put assays and for mass spectrometry.

20 Claims, 30 Drawing Sheets

SEQUENCE LISTING

<160> NUMBER OF SEQ ID NOS: 2

<210> SEQ ID NO 1
<211> LENGTH: 14
<212> TYPE: PRT
<213> ORGANISM: Bovine

<400> SEQUENCE: 1

Val Pro Gln Leu Glu Ile Val Pro Asn Ser Ala Glu Glu Arg
1               5                   10

<210> SEQ ID NO 2
<211> LENGTH: 16
<212> TYPE: PRT
<213> ORGANISM: Bovine

<400> SEQUENCE: 2

Phe Gln Ser Glu Glu Gln Gln Gln Thr Glu Asp Glu Leu Gln Asp Lys
1               5                   10                  15

REAGENTS AND METHODS FOR PHOSPHORYLATION/DEPHOSPHORYLATION ANALYSES

CROSS REFERENCE TO RELATED APPLICATION

This application is a U.S. National Stage patent application of PCT/US2011/032331, which designated the United States, filed Apr. 13, 2011, which claims the benefit of U.S. Provisional Application No. 61/323,442, filed Apr. 13, 2010, and U.S. Provisional Application No. 61/416,714, filed Nov. 23, 2010, the disclosures of which are expressly incorporated herein by reference.

STATEMENT OF GOVERNMENT RIGHTS

This invention was made with government support under CAR0645020 awarded by the National Science Foundation (NSF). The government has certain rights in the invention.

SEQUENCE LISTING

SEQ. ID NO. 1. Polypeptide VPQLEIVPNpSAEER. A portion of bovine α-casein protein that includes a phosphorylated serine residue; this sequence was determined using the reagents and techniques disclosed herein.

SEQ. ID NO. 2. Polypeptide FQpSEEQQTEDELQDK. A portion of bovine β-casein protein that includes a phosphorylated serine residue; this sequence was determined using the reagents and techniques disclosed herein.

FIELD OF THE INVENTION

The invention relates generally to reagents that have a high affinity for phosphorylated molecules and methods for using these reagents to detect and/or enrich samples in phosphorylated molecules.

BACKGROUND

The detailed examinations of cell signaling pathways have become the focus of numerous research groups. Successful completion of such analyses will provide an immense amount of knowledge about the cellular processes and their misregulation, and offer numerous putative drug targets for many heretofore untreatable diseases. A vast majority of these signaling networks depend largely on protein phosphorylation, an essential post-translational modification that regulates numerous cellular functions, including cell cycle progression, proliferation, differentiation, signal transduction and apoptosis. Hunter, T. (2000) Signaling—2000 and beyond, *Cell.* 100, 113-127. It has been shown to be among the most widespread post-translational modifications known. In cells changes in phosphorylation dynamics within the cell have been linked to the onset and development of numerous diseases, most notably cancer. Blume-Jensen, P., and Hunter, T. (2001) Oncogenic kinase signalling, *Nature.* 411, 355-365. Consequently, detection of protein phosphorylation is very important for further understanding of an organism's signaling pathways to prevent such abnormalities.

Currently, one of the most common techniques used to analyze protein phosphorylation is through mass spectrometry. Aebersold, R., and Goodlett, D. R. (2001) Mass spectrometry in proteomics, *Chem Rev.* 101, 269-295. Mann, M., and Jensen, O. N. (2003) Proteomic analysis of post-translational modifications, *Nat Biotechnol.* 21, 255-261. This allows identification of novel phosphorylated proteins and even the sites of phosphorylation. Mass spectrometry, however, is biased toward some phosphorylated sites over others, thus complete analysis of the system is difficult. Furthermore, many groups do not have access to such an instrument due to high cost and the requirement for technical operating experience. The most commonly used methods in this category include the utilization of phospho-specific antibodies and $^{32}P$ labeling in a Western blot or ELISA formats. Though there are phospho-specific antibodies available for purchase, to date, only general anti-phosphotyrosine antibodies are of high quality. Pandey, A., Podtelejnikov, A. V., Blagoev, B., Bustelo, X. R., Mann, M., and Lodish, H. F. (2000) Analysis of receptor signaling pathways by mass spectrometry: identification of vav-2 as a substrate of the epidermal and platelet-derived growth factor receptors, *Proc Natl Acad Sci USA.* 97, 179-184. Phosphoserine and phosphothreonine residues detection is still sequence-dependant, resulting in partiality of these antibodies. As for the $^{32}P$ labeling, although it has been vigorously employed for detection of phosphorylation experiments, the approach has a number of drawbacks, most familiar including working with dangerous radioactive materials and difficulty of identifying physiological phosphorylation. This arises from toxic effects $^{32}P$ has on cells, inducing DNA fragmentation, changing cell morphology, causing cell cycle arrest and eventually resulting in apoptosis. Cooper, P. C., and Burgess, A. W. (1985) Biosynthetic labeling with $^{32}P$: radiation damage to mammalian cells, *Analytical biochemistry.* 144, 329-335. Hu, V. W, and Heikka, D. S. (2000) Radiolabeling revisited: metabolic labeling with (35)S-methionine inhibits cell cycle progression, proliferation, and survival, *Faseb J.* 14, 448-454. As a result, radioactive analyses of protein phosphorylation are more commonly carried out in vitro. To address the disadvantages of the current phosphoprotein detection methods, we introduce a novel soluble nanopolymer-based reagent for the detection of protein phosphorylation in a 96-well plate. Due to such drawbacks, there exists a need to simpler techniques that allows for the determination of protein of phosphorylation states. Some aspects of the instant invention seek to address this need.

SUMMARY OF THE INVENTION

The present invention relates to reagents, kits, and procedures for the analysis of phosphate-containing molecules on the solid phase formats such as well plates, gels, and membranes. Some embodiments of the invention include procedures that resemble ELISA for phosphorylation without the use of phospho-specific antibodies. Some embodiments of the invention include reagents that comprise specific phosphate-recognizing moieties, reporting groups that facilitate detection using fluorophores or spectrometric techniques, and handle groups that may be used to isolate phosphate-containing molecules or attach them to surfaces. Additional uses include purifying reagent bound phosphorylated protein or peptide for follow-up mass spectrometric analyses. Major applications include, but not limited to, quantitative phosphorylation measurement, determination of phosphorylation status, identification of phosphorylation sites, phosphorylation stoichiometric determination, in vitro kinase assay, kinase and phosphase activity assay, and kinase/phosphatase inhibitors screening using the ELISA format.

Some aspects of the invention include reagents for the detection and/or measurement and/or at least partial purification of phosphorylated molecules. In some embodiments the reagent comprises a linking core, a plurality of moieties that include a metal such as a metal ion and or metal oxide and at least one reporter group, wherein the moiety that includes the metal binds to a phosphorylated molecule. Metals that can be used to practice the invention may include metals selected from the group consisting of: Ti(IV), Zr(IV), Fe(III), Ga(IV), Al(III), Sn(IV), Cu(II), and Zn(II). In some embodiments the metal selected from the group consisting of titanium or zirconium. And in some embodiments the moiety that includes the metal is titania. Many of the inventive embodiments include linking core which is a nanopolymer in many embodiments the nanopolymer is a dendrimer molecule. In some embodiments at least a portion of the metal may be in the form of an ion or a metal oxide. Forms of metal that can be used to synthesize the phosphate binding reagent include, but are not limited to, titania and zirconia.

Still other embodiments of the reagent include a linking core or linking group that connects a reporter group and a group that readily binds to phosphorylated molecules. These linker moieties may include an amide moiety. In some embodiments the amide including group is selected from the group consisting of: lysine, di(lysine) and poly(lysine). In some embodiments the reagent has a molecular weight of less than about 1000 daltons. In some embodiments at least one reporting group may be directly attached to a moiety that binds to phosphate molecules.

In some embodiments the reagent includes a nanopolymer comprising at least one dendrimer molecule. These reagents are suitable for methods that include binding phosphorylated molecules further use such as for analyses by method such as mass spectrometry. In some embodiments these reagents may include at least one moiety that docks the reagent to a surface or to another sometime larger chemical entity.

In some embodiments the dendrimer in the linking core or linking groups comprises at least 32 surface groups. In still other embodiments the number of dendrimer surface groups is less than 32.

In some embodiment of the invention the ratio of moieties that include either metals such as titanium and zirconium and the reporter groups in the reagent is in the range of about from about 2:1 to about 1:5. In some embodiments the phosphate binding reagent includes from about 10 to about 20 metal groups and from about 20 to about 40 reporter groups. In some embodiments the number of phosphate binding groups that include a metal such as titanium and the like and the number of reporting groups are independently selected so as to maximize binding and/or the generation of detectable signal.

In some embodiments the reporter group in the reagent is selected from the group consisting of: biotin, an antibody, a lectin, a thiol, a fluorescent group, a chromophore, a chemiluminescent group, a radioactive group and the like. Virtually any chemical group that generates a detectable signal can be attached to the phosphate binding group either directly or through a linking core or core linking group to form a reagent in conformity with the disclosed invention.

In some embodiments the reagent for binding phosphorylated molecules further include at least one handle group. The handle group may be attached to the core linker or linking group or it may be directly attached to either or both the reporter moiety or to the group that binds the phosphorylated molecules.

Still other aspects of the invention include methods for the detection and/or measurement and/or at least partial purification of phosphorylated molecules many of these methods comprise the steps of: contacting a reagent such as those disclosed and implied herein that bind to phosphorylated molecules with a sample. The reagent used in many of these methods are comprised of a linking core or linking group, a plurality of metal oxide groups and at least one reporter group, in these reagents the metal oxides binds to a phosphorylated molecule, such that at least a portion of the reagent binds to a portion of the sample. Additional steps in these methods may include removing at least a portion of any unbound reagent; and detecting the phosphorylated molecules in the sample by detecting the reporter groups of the regent or using the reagent bound to the phosphorylated molecules as a means for retrieving the phosphorylated molecules from the sample. In some embodiments of the methods, the moiety that binds the phosphate and/or phosphorylated molecule include at least one metal selected from the group consisting of: Ti(IV), Zr(IV), Fe(III), Ga(IV), Al(III), Sn(IV), Cu(II), and Zn(II). In some embodiments the metal is selected from the group consisting of titanium or zirconium. And in still other embodiments of the invention the moiety in the reagent that has the highest binding affinity for the phosphorylated molecule is titania.

In some embodiments of the invention the linking core or core groups in the reagent used to practice the inventive methods is a nanopolymer. In some embodiments the nanopolymer in the linker core is dendrimer molecule. In some embodiments the dendrimer in the linking core or linking groups comprises at least 32 surface groups. In still other embodiments the number of dendrimer surface groups is less than 32.

In some embodiment of the invention the ratio of titania or zirconia groups and the reporter groups in the reagent used to practice the methods of the invention is in the range of about from about 2:1 to about 1:5. In some embodiments the phosphate binding reagent includes from about 10 to about 20 titania or zirconia groups and from about 20 to about 40 reporter groups. In some embodiments the number of phosphate binding groups such as titania and the like and the number of reporting groups are independently selected so as to maximize binding and/or the generation of detectable signal.

In some embodiments of the inventive methods the linking core or core group in the reagents used to practice the invention includes an amide moiety. In some embodiments the linking core or linking groups includes at least one group selected from the group consisting of: lysine, di(lysine) and poly(lysine). In some embodiments of the method the reagent has a molecular weight of less than about 1000 daltons.

In some of the inventive methods the sample that is contacted with the reagent comprises cells, tissue, proteins, lipids or combinations thereof. In some embodiments the samples are subjected to various processing steps before they are contacted with the inventive reagent. Such pre-reagent contact steps include, but are not limited to, whole or partial purification, heating, freezing, or storage and the like.

In some embodiments the inventive methods further includes at least one procedure selected from the group consisting of: Western blotting, fluorescent imaging, chemiluminescence detection, spectrophotometric detection, high-through put screening; mass spectrometric analysis, in-gel staining, in vitro kinase assays, or in vivo phosphorylation analysis. In some embodiments the inventive reagent is contacted with a portion of the sample in a vessel such as a cuvett, test tube, tier plate and the like.

In some embodiments of the invention the reagent used to practice the invention includes a linker core that comprises a dendrimer having at least 32 surface groups. In still other methods the dendrimer acting as the linking group as less than 32 surface groups. In some embodiments the ratio of the moieties that include titanium or zirconium and reporter groups in the reagent used to practice the inventive methods is from about 2:1 to about 1:5. In still other embodiments the reagent includes about 10 to about 20 moieties that include either titanium or zirconium and from about 20 to about 40 reporter groups. Samples that may be used to practice the invention include, but are not limited to, samples that have phosphate bound to proteins, peptides, polypeptides, nucleic acids, components of cell membranes and the like.

In some embodiments the reporter group in the reagent used to practice the inventive methods is selected from the groups consisting of: biotin, an antibody, a lectin, a thiol, a fluorescent group, a chromophore, a chemiluminescent group, a radioactive group and the like.

Still other aspects of the invention include kits for the detection and/or measurement and/or at least partial purification of phosphorylated molecules. Kits in conformity with these embodiments may include at least one reagent in conformity with the reagents and/or methods disclosed. Reagents in these kits may that bind to a phosphorylated molecule, a core linker or linker groups and a moiety that produces a signal in a sample comprising a reagent said reagent comprising a linking core, a plurality of metal oxide groups and at least one reporter group, wherein the metal oxides binds to at phosphorylated molecule.

DESCRIPTION

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates.

Unless stated or clearly implied otherwise the term 'about' as used herein is meant to encompass a range of values of plus or minus 10 percent. For example, about 1.0 includes values from 0.9 to 1.1.

Figure 1:
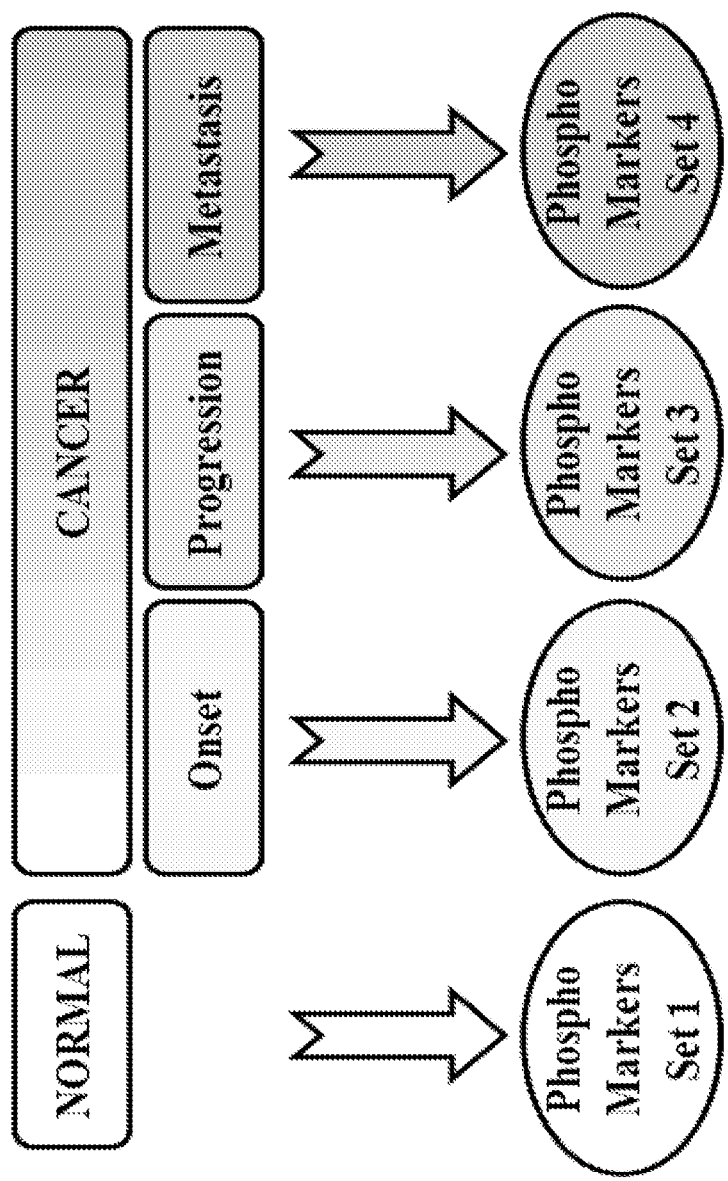
FIG. 1. Illustration showing changes in the phosphorylation states of some enzymes as cells transform from normal cells into metastatic cells.

Determining the phosphorylation states of various enzymes have important implication for a wide variety of disciplines including, but not limited to, cellular biology, biochemistry, molecular biology, agronomy, microbiology, human and animal health and the like. See for example, FIG. 1, which illustrates how the phosphorylation states of various proteins may change overtime as cell morphs from normal to cancerous. Some of the compositions and methods of using these compositions include linking a group that preferentially or even selectively interacts with phosphate groups to a reporting moiety. Various embodiments can be constructed and can be adapted to study the phosphorylation state of a wide variety of proteins and polypeptides. Broadly, the present invention provides a reagent for the detection of phosphorylated molecules comprising a nanopolymer core, a plurality of titanium or zirconium groups and a plurality of reporter groups. It has been found that the plurality of titanium or zirconium groups provides selective and sensitive binding to the phosphate moieties of the phosphorylated molecules. The reporter groups may be any reporter group known in the art appropriate for the method in which the reagent is used. The present application also provides methods for using the reagent of the present invention to detect phosphorylated molecules. The method may include the steps of adding the reagent to a sample and incubating the reagent with the sample, allowing the reagent to bind to the phosphate moieties of the phosphorylated molecule. The excess reagent is then removed and the bound reagent is detected. Still other methods provided herein can be used to determine the phosphorylation site of a given polypeptide, protein and or peptide by analyzing a portion of a sample attached to the inventive reagent by mass spectrometry, see for example the scheme of FIG. 19.

The selective and sensitive binding of the reagent to phosphate moieties allows for the determination of the presence of phosphorylated molecules without the problems of current assays, such as lack of sensitivity, false positives and high background signals.

In one embodiment of the present invention there is provided a reagent with a nanopolymer core, a plurality of titanium or zirconium groups and a plurality of reporter groups. The nanopolymer core may be a dendrimer. Dendrimers are highly ordered, hyperbranched and polyfunctional macromolecules. Dendrimers have a core region and surface groups where the surface groups may react with other molecules to functionalize the dendrimer. The dendrimer may be a global or "starburst" shape or it may be linear. Non-limiting examples of dendrimers are polyamidoamine dendrimers (PAMAM), polypropylenimine dendrimers, or poly(aryl ether) dendrimers. The surface groups of the dendrimers may be, but not limited to, primary amino, carboxylate or hydroxyl groups. The choice of dendrimer and surface group will depend on the application and the groups to be attached to the dendrimer. The choice of a dendrimer is within the scope of the skilled artisan's knowledge.

Dendrimers contain a plurality of surface groups, usually in multiples of 4. The number of surface groups will determine, and may even limit the number of titanium groups and reporter groups that can be bound to the dendrimer nanopolymer core. In one illustrative embodiment the number of surface groups is from about 32 to about 128. In an alternate illustrative embodiment, the number of surface groups is at least 32.

In an alternate embodiment, the nanopolymer may be a linear polymer, such as, but not limited to, polyallyic amine or polylysine. The nanopolymer may have surface groups such as primary amino, hydroxyl or carboxylate groups. As with the dendrimer nanopolymers, the number of surface groups may determine the number of titanium groups and reporter groups on the nanopolymer.

In another embodiment the reagent of the present invention comprises a plurality of reporter groups. The reporter groups are groups that allow for the detection of the bound reagent to the phosphorylated molecules. Reporter groups are well known in the art and may be used with the present invention. In one illustrative embodiment, the reporter group is part of a conjugate pair. In the conjugate pair a second molecule, the detection group, binds to the reporter group. The detection group further comprises a moiety for visualizing or detection the reporter group. A well known conjugate pair is biotin (reporter molecule) and avidin-HRP (detection group) where the avidin is modified with horse radish peroxidase. After binding the avidin to the biotin, substrates for HRP are added and the presence of the reporter group assayed. Other well known conjugate pairs are antibody and antigens, alkynyl and azide, lectin and carbohydrates, hydrazine and aldehyde, iodoacetyl and thiol, maleimide and thiol or combinations thereof. The detection group can be modified with a florescent molecule, a chromophore, a chemiluminescent molecule or a radioactive molecule or atom.

Alternatively, the reporter group may be directly modified with a compound that allows for detection of the reporter molecule in a sample. The reporter group may be modified with a fluorescent molecule, a chemiluminescent molecule or a radioactive molecule or atom.

The ratio or amount of titanium groups to reporter groups may also be considered. The actual number of moieties that include metals such as titanium groups may affect the sensitivity of the binding to the phosphate moieties of the phosphorylated molecules. The more phosphate biding groups, the more sensitive the reagent is binding to phosphorylated molecules. Alternatively the number of reporter molecules may affect the sensitivity of the detection of the labeled phosphate moieties. In some illustrative embodiments, the reagent may have from about 10 to about 20 titanium groups. In some alternate illustrative embodiments, the reagent may have from about 20 to about 40 reporter groups. In another embodiment the ratio of titanium groups to reporter groups may be from about 2:1 to 1:5.

In some alternate embodiments of the present invention there is provided a reagent with a core, at least one titanium or zirconium group and at least one reporter group. The reagent may further comprise a handle group if desired. The reagent has a molecular weight of less than about 1000 Daltons. The core may comprise small molecules such as, but not limited to, lysine or poly(lysine). Alternatively, the reagent may simply comprise at least one titanium or zirconium group bound to a reporter group. In one embodiment, the titanium or zirconium group may be attached to the core or reporter group directly or it may be attached to a ligand where the ligand is directly bound to the core or reporter group. It will be appreciate that the smaller reagents allow the visualization of phosphorylated species directly on a gel followed by the identification of phosphorylation sites by mass spectrometry analyses. The smaller size allows the reagent to penetrate directly into agarose or polyacrymide gels to achieve direct in-gel staining.

In one illustrative embodiment of the present invention, the reagent may be used for analysis of nucleic acids. The reagents, particularly the small reagents, can effectively address two issues in nucleic acid analysis. First, the reagent may replace the carcinogenic ethidium bromide (EtBr) for safer and more sensitive staining of nucleic acids in polyacrylamide or agarose gels. Second, for certain nucleic acids that are difficult to amplify (i.e., direct PCR does not work for small cDNA and small RNAs), the reagent may greatly enhance the sensitivity for direct detection of nucleic acids in the gel as the reagent may bind to every nucleotide in the nucleic acids in the gel as the reagent may bind to every nucleotide in the nucleic acid.

In another illustrative embodiment, the reagent may be used for analyses of phosphoproteins. Direct in-gel detection of phosphorylated molecules (i.e., proteins or nucleic acids) is extremely appealing, because transferring the phosphorylated molecules from the gel is not always efficient for certain proteins and the procedure is tedious. The reagent allows for detection of phosphorylated proteins in the gel at high sensitivity and selectivity. Moreover, the inclusion of a handle group facilitates follow-up in-gel digestion and mass spectrometry analysis for the identification of phosphoproteins and phosphorylation sites. In particular, the small size of the small reagent assures easy access to the proteins and fast removal after staining is complete. The stained phosphoprotein band can be cut out of the gel, digested, and phosphopeptides isolated using the handle group, followed by mass spectrometry analysis for protein identification and phosphosite localization. In still other embodiments, the phosphorylated molecule may be attached to a surface such as the surface of a micro-titer plate and contacted with a reagent such as pIMAGO. Phosphorylated molecules attached to the reagent may be assayed using mass spectrometry. If the phosphorylated sample is a peptide, protein or polypeptide these methods can be adapted to enable the determination of the amino acid sequence of at least a portion of the sample bound to the reagent.

In yet another illustrative embodiment, the reagent of the present invention may be used in analysis of phospholipids. The phospholipid bilayer is a very unique structure and an integrated part of the cell. The high specificity of reagent allows imaging of phospholipids on a living cell to monitor cell membrane functions. In vitro characterization of phospholipids can be achieved by isolation of the labeled phospholipids from the cell membrane followed by mass spectrometric analysis.

In a further embodiment, the present invention further comprises a handle group also referred to a control handle group. The handle group is a chemical moiety that allows for the subsequent facile isolation of the labeled phosphorylated molecule. Once a labeled phosphorylated molecule has been detected, it may be desirable to isolate the phosphorylated molecule so that it may be identified. In the case of a phosphoprotein, the phosphoprotein may be subject to proteolysis and the phosphorylated peptide fragment may be isolated using the handle group of the reagent. Non-limiting examples of handle groups may be alkyne or azide (click chemistry), hydrazide or aldehyde (hydrazine chemistry), iodoacetyl or thiol, or, maleimide or thiol. In some embodiments the handle may be used to attach the reagent to a surface. In some of these embodiments the reagent can be used to capture phosphorylated molecules.

In one embodiment, the present invention further provides methods for using the reagent of the present invention to detect phosphorylated molecules in a sample. Although there is no limit to the definition of a phosphorylated molecule other than a molecules comprising at least one phosphate group, some non-limiting example of phosphorylated molecules are phosphoproteins and phospholipids.

The method may include the steps of adding a reagent to the sample, incubating the sample and the reagent, allowing the reagent to react with the phosphorylated molecules in the sample, wherein the reagent binds to the phosphorylated molecules, removing any unbound reagent and detecting the phosphorylated molecules in the sample by detecting the reporter groups of the reagent. The method may be, but not limited to, Western blotting, fluorescent imaging, in-gel staining, in vitro kinase assay or in vivo phosphorylation analysis. The sample may comprise cells, tissue, isolated proteins or lipids, lysed cells, a gel or any other medium in which it is desired to assay for phosphorylated molecules.

The amount of reagent required may depend on the size of the sample and the number of metal including groups that bind to phosphorylated molecules and/or the number of reporter groups on the nanopolymer core as well as the detection method. If a given pIMAGO reagent has a larger number of metal including moieties that bind to phosphorylated molecules it may be possible to use less reagent of the reagent to bind to a given phosphorylated molecule in a sample. In one illustrative embodiment, the amount of reagent in the sample may be from about 5 uM to about 20 uM. The optimal amount of reagent may be determined by the skilled artisan without undue experimentation.

One approach disclosed herein provides reagents that can be used in a procedure that is similar to Enzyme-Linked-ImmunoSorbent Assay (ELISA)-type analyses. ELISA assays have long been used to successful identify and measure of biological molecules and their activities. Engvall, E., and Perlmann, P. (1971) Enzyme-linked immunosorbent assay (ELISA). Quantitative assay of immunoglobulin G, *Immunochemistry.* 8, 871-874. There are a number of different types of ELISA. The three most commonly used include direct, indirect, and sandwich ELISA. In direct ELISA, an antigen is attached directly to the plate, and a labeled antibody is then introduced, allowing immediate read-out. Similar to direct, in indirect ELISA an antigen is attached to the plate, but then an unlabeled antibody is allowed to react with it. This method requires the use of a labeled secondary antibody, which makes this approach more cost-effective since only a handful of labeled secondary antibodies need to be purchased. The third common method, sandwich ELISA, is perhaps the most selective because the antigen is attached to its antibody immobilized on a plate, ensuring that only the protein of interest is bound. Therefore, the procedure allows for analyses of more complex samples. In each case, the above assays are rapid, sensitive, reproducible, easy to perform, and are particularly useful for high-throughput screening experiments. Thus, their utility is immense. Though quantitation of protein amount is probably the most common use for ELISA, recently, many kits have been developed to study protein post-translational modifications, most commonly phosphorylation.

In the recent years, many ELISA-type procedures have been developed for protein phosphorylation analyses. Bianco, C., Giovannetti, E., $C_1$.ardiello, F., Mey, V., Nannizzi, S., Tortora, G., Troiani, T., Pasqualetti, F., Eckhardt, G., de Liguoro, M., Ricciardi, S., Del Tacca, M., Raben, D., Cionini, L., and Danesi, R. (2006) Synergistic antitumor activity of ZD6474, an inhibitor of vascular endothelial growth factor receptor and epidermal growth factor receptor signaling, with gemcitabine and ionizing radiation against pancreatic cancer, Clin Cancer Res. 12, 7099-7107. Carter, T. A., Wodicka, L. M., Shah, N. P., Velasco, A. M., Fabian, M. A., Treiber, D. K., Milanov, Z. V., Atteridge, C. E., Biggs, W. H., 3rd, Edeen, P. T., Floyd, M., Ford, J. M., Grotzfeld, R. M., Herrgard, S., Insko, D. E., Mehta, S. A., Patel, H. K., Pao, W., Sawyers, C. L., Varmus, H., Zarrinkar, P. P., and Lockhart, D. J. (2005) Inhibition of drug-resistant mutants of ABL, KIT, and EGF receptor kinases, Proc Natl Acad Sci USA. 102, 11011-11016. Rani, C. S., Qiang, M., and Ticku, M. K. (2005) Potential role of cAMP response element-binding protein in ethanol-induced N-methyl-D-aspartate receptor 2B subunit gene transcription in fetal mouse cortical cells, Molecular pharmacology. 67, 2126-2136. They range from immobilizing a peptide substrate to assess kinase activity, Yu, J. S., Chang, S. H., Chan, W. H., and Chen, H. C. (2001) Enzyme-linked immunosorbent assay for the determination of p21-activated kinase activity, J. Biochem. 129, 243-251., to utilizing a phosphosite specific antibody. Pattoli, M. A., MacMaster, J. F., Gregor, K. R., and Burke, J. R. (2005) Collagen and aggrecan degradation is blocked in interleukin-1-treated cartilage explants by an inhibitor of IkappaB kinase through suppression of metalloproteinase expression, J Pharmacol Exp Ther. 315, 382-388. The latter approach has gained particular popularity because it can be used to easily assess protein phosphorylation directly or to carry out indirect analyses of kinase and phosphatase activities. In this method, a general antibody for the protein of interest is immobilized on a solid-phase support and then incubated with a sample mixture containing the antigen. After antigen binding and washing, a phospho-antibody is added that is specific to the antigen's site of phosphorylation. Thus, any signal produced is due to the presence of phosphorylation at that particular site. Besides just qualitative observation, the technique also allows for quantitative measurement of phosphorylation (sometimes absolute) in comparison to total amount of protein present, provided that a phosphorylated standard is available.

Despite the usefulness of the currently available phospho-ELISA methods, they are not always practical. First of all, in order to use the assay, the site of phosphorylation of interest has to be known beforehand, thus limiting the analysis to only well-characterized phosphorylation events. Second, a working phosphosite-specific antibody has to be made for every single phosphosite and phosphoprotein, making the assays very costly and difficult if the antibody is unavailable. Though good general phosphotyrosine antibodies are accessible for use, no successful phosphoserine or phosphothreonine antibodies exist that are non-specific to certain motifs.

The non-antibody-based reagent disclosed herein is capable of detecting a phospho-protein without any prejudice toward or against certain motifs or sites of phosphorylation thereby alleviating many of the problems with the existing antibody based assays. Various forms of the reagents that bind phosphorylated molecules and are described or inferred herein may be referred to herein as pIMAGO. One embodiment of pIMAGO is a reagent is based on a soluble polyamino-amine nanopolymer (dendrimer) that has been functionalized with titanium groups for selective binding to phosphorylated residues and with biotin molecules for easy detection. Besides solubility, the advantages of using dendrimers include their high structural and chemical homogeneity, compact spherical shape, and controlled surface functionalities. Boas, U., and Heegaard, P. M. (2004) Dendrimers in drug research, Chem Soc Rev. 33, 43-63. Titanium was used to immobilize the nanopolymer because it has been demonstrated to possess superior selectivity towards phosphorylated residues. Larsen, M. R., Thingholm, T. E., Jensen, O. N., Roepstorff P., and Jorgensen, T. J. (2005) Highly selective enrichment of phosphorylated peptides from peptide mixtures using titanium dioxide microcolumns, Mol Cell Proteomics. 4, 873-886. Pinkse, M. W, Uitto, P. M., Hilhorst, M. J., Ooms, B., and Heck, A. J. (2004) Selective isolation at the femtomole level of phosphopeptides from proteolytic digests using 2D-NanoLC-ESI-MS/MS and titanium oxide precolumns, Anal Chem. 76, 3935-3943. Experiments, including those disclosed herein have demonstrated the unparallel utility of titanium-based enrichment under homogeneous conditions. The soluble nanopolymer (dendrimer) functionalized with multivalent Ti metal ions (termed PolyMAC) was used for phosphopeptide enrichment from a complex whole cell lysate digest, demonstrating outstaining selectivity, reproducibility, and high recovery. Iliuk, A. B., Martin, V. A., Alicie, B. M., Geahlen, R. L., and Tao, W. A. (2010) In-depth analyses of kinase-dependent tyrosine phosphoproteomes based on metal ion functionalized soluble nanopolymers, Mol Cell Proteomics, ePub.

Some embodiments of the invention, introduce a procedure that is similar to ELISA without the use of phosphor-specific antibodies. In some embodiments, the procedure may use the reagents, termed pIMAGO (phosphor-imaging), for the specific detection of phosphate-containing molecules. One demonstration of this invention is its application with phosphoproteins using standard 96-well plates but it is conceivable that it is also applicable to other phosphate-containing molecules such as phospholipids and nucleic acids.

Figure 2A:
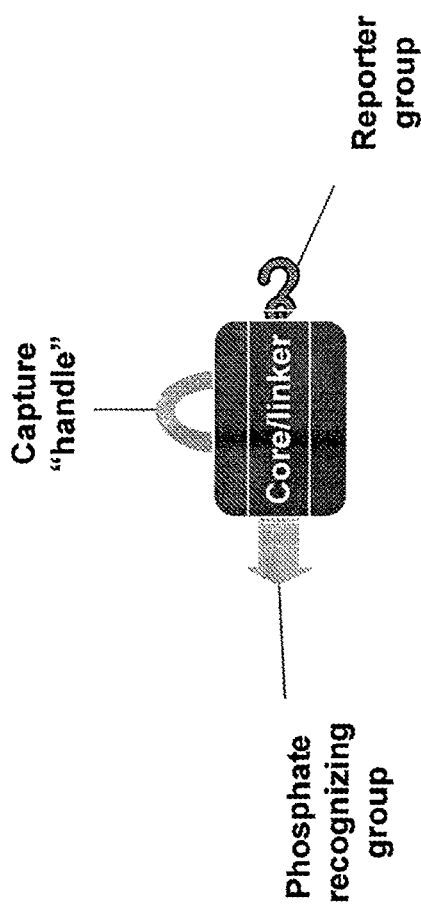
FIG. 2A. Illustration of a reagent suitable for detecting the presence of a phosphorylated protein.
Figure 2B:
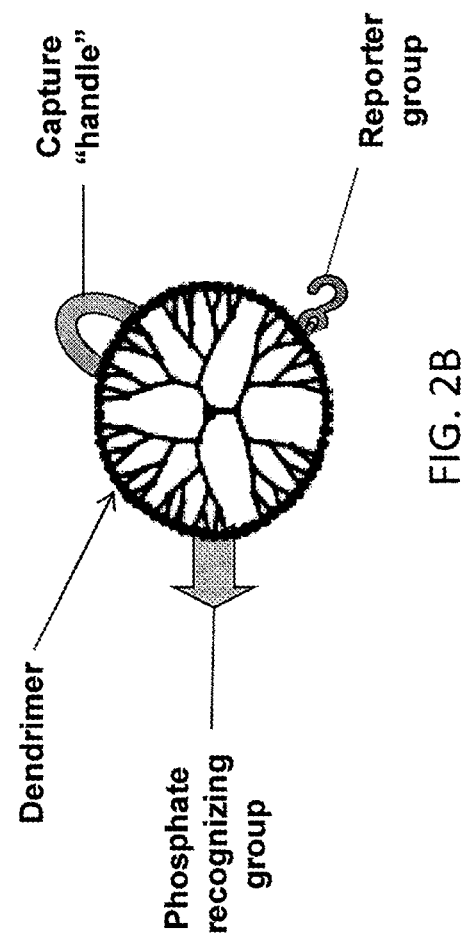
FIG. 2B. Illustration of a representative reagent that includes a dendrimer core linker and is suitable for binding to phosphorylated proteins.

Referring now to FIG. 2A, some embodiments include reagent for detecting phosphorylated polypeptides wherein the reagent includes a core linker group that connects a phosphate recognizing group and a reporter group. Some embodiments further include a capture handle that can be used to attach the reagent to a surface or to retrieve labeled phosphorylated molecules from a sample. In some embodiments such as illustrated in FIG. 2B the linking group in the reagent is a dendrimer.

Figure 3A:
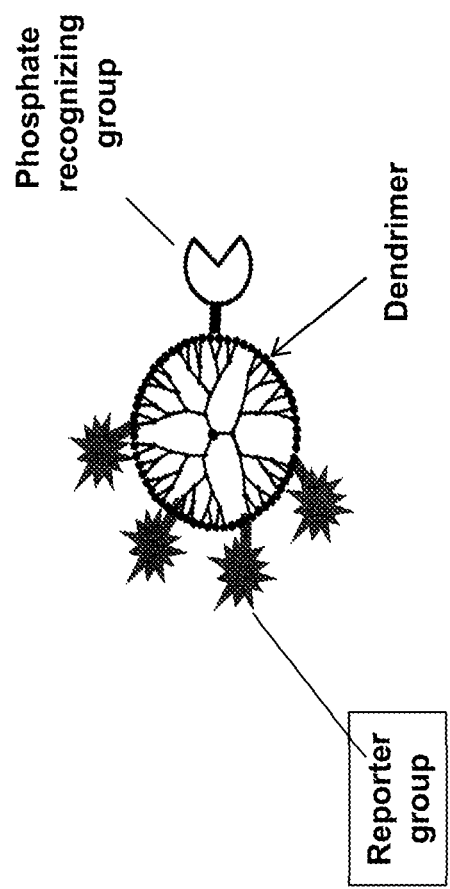
FIG. 3A. Illustration of a reagent for detecting phosphorylated groups that includes a reporter, a phosphate binding group and core linker.
Figure 3B:
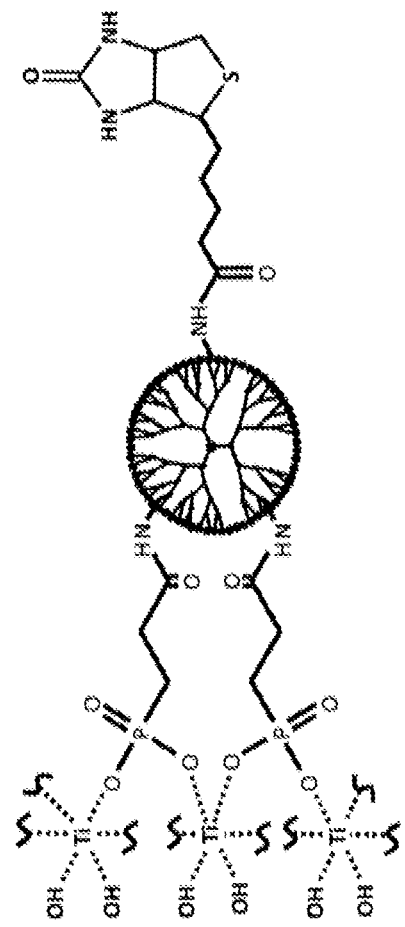
FIG. 3B. Structure of some specific pIMAGO reagents that include biotin, a dendrite core and titania.

Some embodiments, as illustrated in FIG. 3A include a core linker in the form of a dendrimer, a reporter such as a fluorescent, chemiluminescent, radioactive, enzyme, biotin-avidin couple or the like. In some embodiments the reagent, includes a soluble nanopolymer such as polyamidoamine (PAMAM) derivatized with two types of functional groups, a reactive group that binds to phosphorylated molecules specifically, and a reporter group for direct or indirect by spectroscopy detection. One such example illustrated in FIG. 3B, the group that binds the phosphorylated group includes titanium (IV) and the reporter moiety is biotin.

Figure 4A:
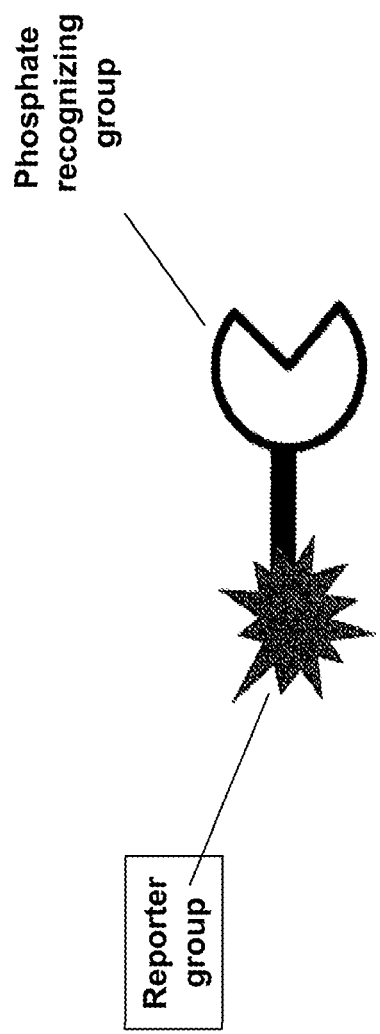
FIG. 4A. Illustration of a small reagent for detecting phosphorylated groups that includes a reporter and a phosphate binding group.
Figure 4B:
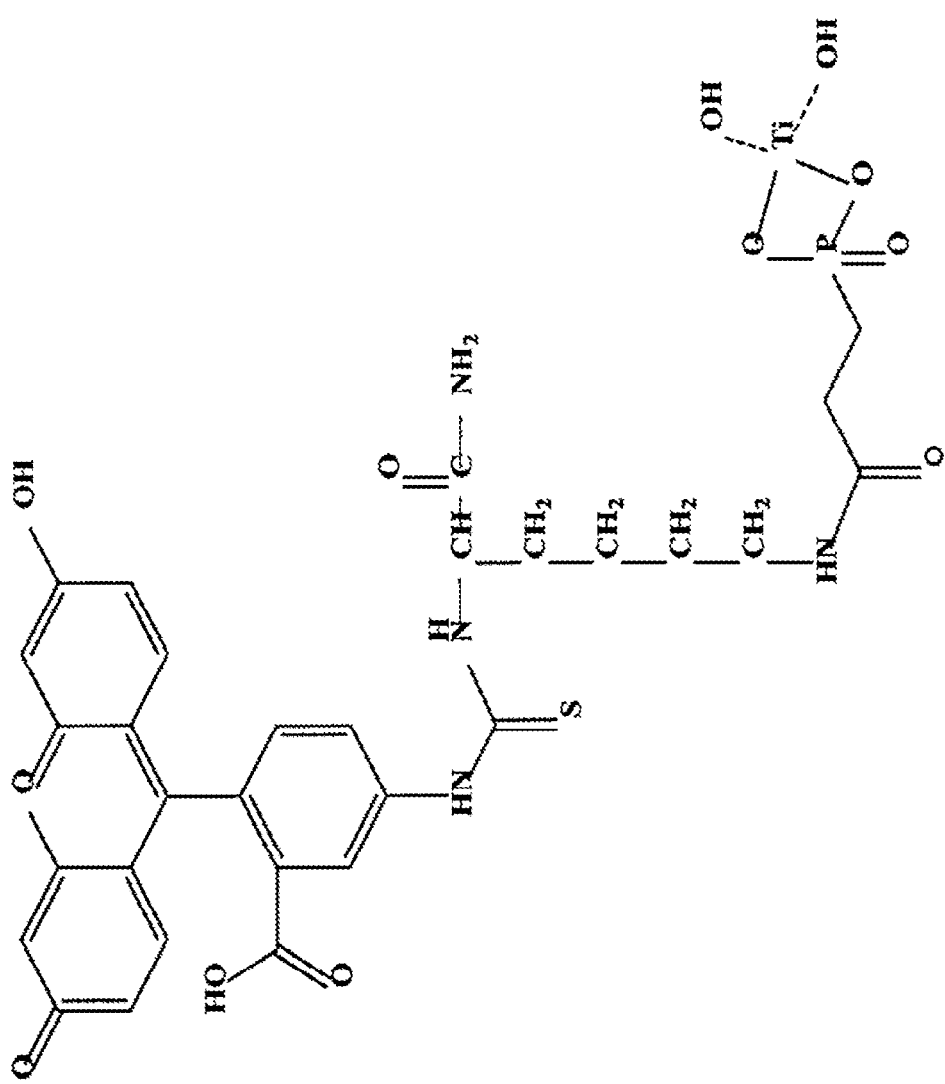
FIG. 4B. Illustration of one example of a small reagent that binds phosphorylated groups.

Referring now to FIG. 4A, in still other embodiments the phosphorylated molecule binding reagent is small molecule-based reagent that includes a reporter group (e.g., a dye or fluorescence tag or the like) and immobilized titanium. One such example of this type of pIMAGO reagent is illustrated in FIG. 4B. In some embodiments the reagent is designed to include a handle group in the molecule, see for the examples summarized in FIGS. 4C and 4D.

The types of reagents exemplified in FIG. 4 are well suited to direct in-gel detection of phosphorylated molecules (i.e., proteins or nucleic acids) is extremely appealing, because the transferring step is not always efficient for certain proteins and the procedure is tedious. The major advantages for these types of reagents include not only direct in-gel staining but also its compatibility with follow-up in-gel digestion and mass spectrometry analysis for the identification of phosphoproteins and phosphorylation sites. The small size of the reagent assures easy access to the proteins or nucleic acids and fast removal after staining is complete. Where advantageous the stained phosphoprotein band can be cut out of the gel, digested, and phosphopeptides isolated using the handle group, followed by mass spectrometry analysis for protein identification and phospho-site localization.

Because pIMAGO based reagents are capable of detecting a wide variety of phosphorylation sites, in many instance only one reagent is needed for all of the phospho-ELISA assays. Therefore, these reagents can be used to not only detect and quantify the phosphorylation level of a protein, but also to examine kinase or phosphatase activities (in vitro or in vivo). Here, a protein of interest can be directly immobilized on a polystyrene plate, or a specific antibody can be bound on a protein A/G containing plate to enable more complex analyses of biologically relevant processes. Because no phosphorylation site knowledge is needed a priori, new phosphorylation discoveries can be made, especially when comparing the levels of phosphorylation of a particular protein under different conditions.

Figure 5A:
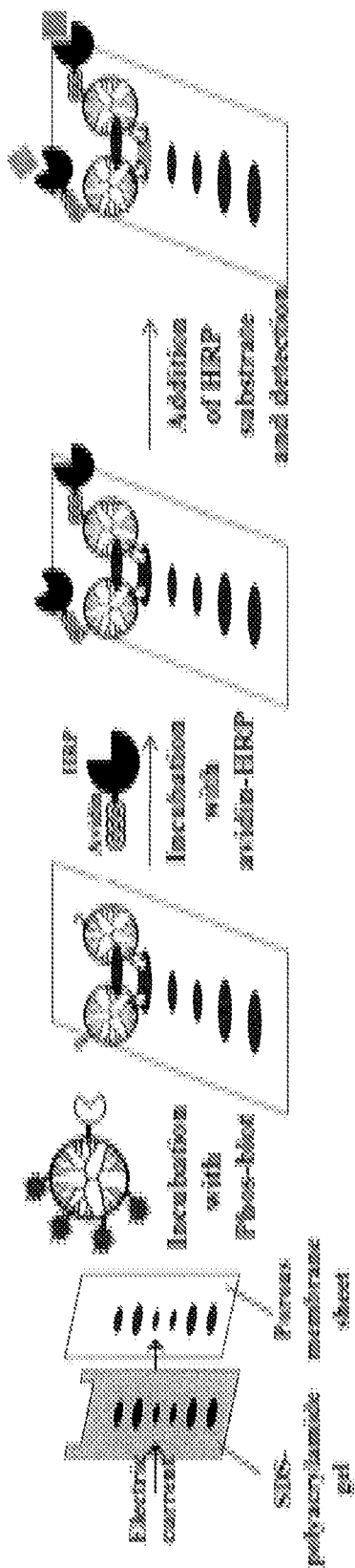
FIG. 5A. Schematic diagram illustrating some steps in the Western blotting using some of the reagents disclosed herein.
Figure 5B:
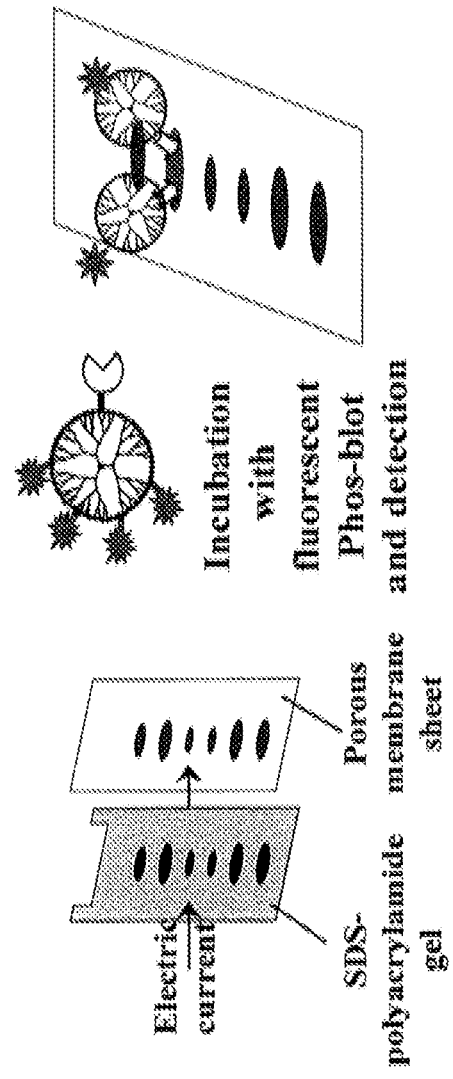
FIG. 5B. Schematic diagram illustrating some steps in the direct detection of phosphomolecules transferred to a porous membrane using some of the reagents disclosed herein.
Figure 6A:
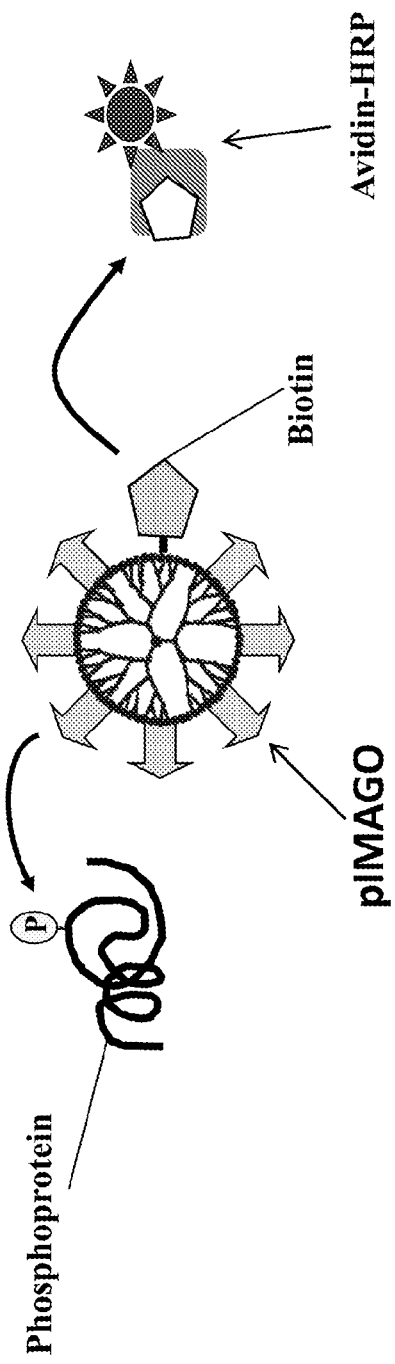
FIG. 6A. Illustration of pIMAGO binding to phosphorylated proteins and an avidin-HRP reporter.
Figure 6B:
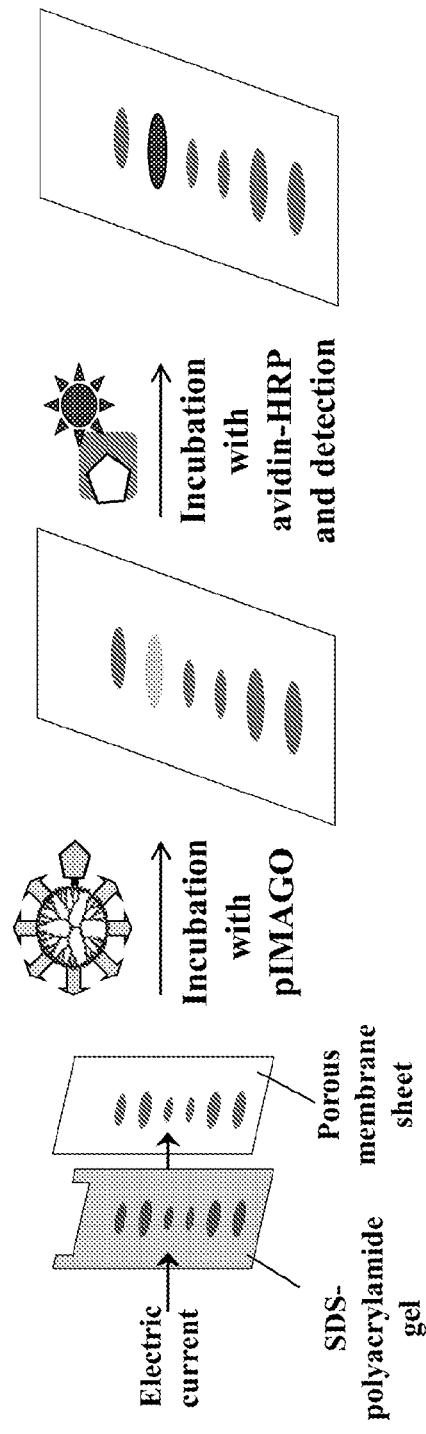
FIG. 6B. Schematic diagram showing steps in pIMAGO analysis of an SDS-PAGE gel.

Referring now to FIG. 5A the steps in a typical Western Blot probed with one of the pIMAGO reagents, a phosphomolecule binding reagents according to some embodiments of the present invention. Next, the membrane is contacted with avidin-HRP and after washing it is assayed for HRP activity. Referring now to FIG. 5B, one very sensitive detection approach is to replace biotin groups with a fluorophore (e.g. fluorescein isothiocyanate (FITC)), thus enabling immediate detection with a regular image scanner after the blotting. If advantageous the two procedures can be used separately or in parallel. The reagents disclosed herein for detecting phosphorylated molecules are well suited for use in high through put screening for phosphorylated molecules. For example, reagents such as pIMAGO can be used in assays based on micro-titer plates. Still another embodiment of the invention uses the high affinity of reagents pIMAGO reagents for phosphorylated molecules to process samples for mass spectrometric analysis. Briefly, a sample may be contacted with one of the phosphate binding reagents once one bound to the reagent the reagent may be used retrieve the portion of the sample that includes phosphorylated moieties and the retrieved portion of the sample may be analyzed by mass spectrometry. In the case of phosphorylated polypeptides, these methods can be used to provide data and the location of phosphorylated amino acid residue in the sample including under some circumstance sequence data in the vicinity of the phosphorylated residue.

The pIMAGO-based detection of phospho-proteins on ELISA plates can be combined with mass spectrometry. The reagent pIMAGO can be additionally functionalized with a "handle" group, enabling capture of the phosphoproteins onto solid phase support, followed by trypsinization and mass spectrometry analysis. Such a combination of phosphoprotein detection, quantitation and identification is an unprecedented approach that would enable a complete examination of protein phosphorylation using just one protocol.

Figure 19:
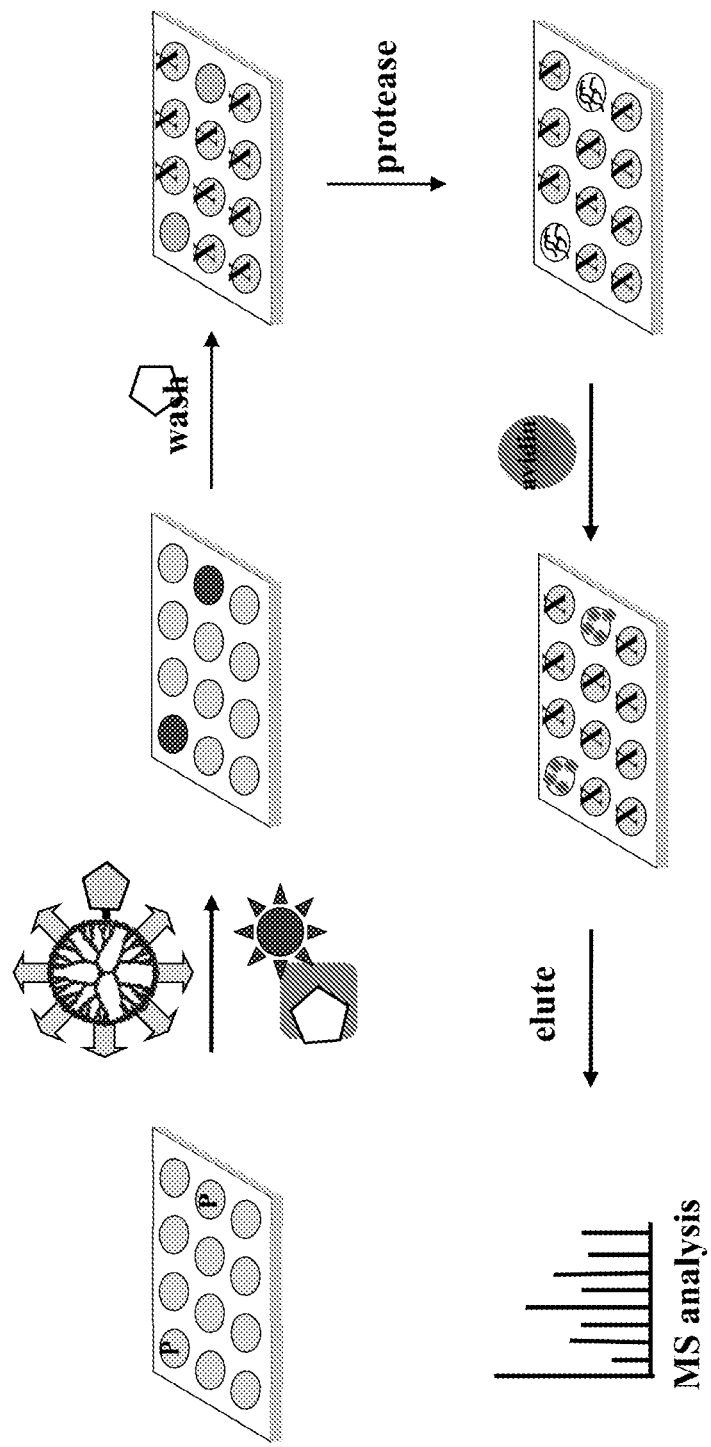
FIG. 19. Schematic illustrating the steps in using a plate based pIMAGO based assay to prepare phosphopeptides for analysis by mass spectrometry.

In some embodiments of the invention pIMAGO is used for a sandwich ELISA-type analysis coupled to mass spectrometry. It is a highly selective approach, in part, because the antigen is attached to its antibody immobilized on a plate, ensuring that only the protein of interest is bound. Therefore, the procedure allows for analyses of complex samples. After coupling of the protein to its antibody, the overall change in phosphorylation can be quantitated using a pIMAGO based reagent. Finally, the phosphoprotein can be digested on-plate, the resulting phosphopeptides further enriched using features of the same pIMAGO reagent, and the sites of phosphorylation on the polypeptide can be analyzed by mass spectrometer various steps in this process are illustrated in FIG. 19. This single method enables the complete examination of protein phosphorylation profile including phosphoprotein detection, quantitation and phosphorylation site detection and sequencing.

Currently available commercially available methods for phosphoprotein detection followed by mass spectral (MS) analysis are inefficient and exhibit low in-gel phosphoprotein staining Fu, Q.; Liu, P. C.; Wang, J. X.; Song, Q. S.; Zhao, X. F. *BMC Genomics* 2009, 10, 600; Crow, T.; Xue-Bian, J. J. *Neuroscience,* 165, 1182-1190; and Ma, M.; Guo, X.; Wang, F.; Zhao, C.; Liu, Z.; Shi, Z.; Wang, Y.; Zhang, P.; Zhang, K.; Wang, N.; Lin, M.; Zhou, Z.; Liu, J.; Li, Q.; Wang, L.; Huo, R.; Sha, J.; Zhou, Q. *J Proteome Res* 2008, 7, 4821-4830. Additionally, these methods require that the immunoprecipitated proteins be run on a gel (most on a 2D gel), followed by in-gel digestion of every band of interest, steps which make this approach time and energy intensive. The procedure disclosed eliminates these cumbersome constraints by affording a single step protein purification and immobilization. Additionally, the same pIMAGO reagents are used for detection and sequential phosphopeptide enrichment, making the overall approach more efficient. This approach disclosed herein is also well suited for automation. In various embodiments pIMAGO-based sandwich ELISA assays are capable of selectively detecting phosphorylated proteins without disrupting the protein-antibody interactions.

Figure 11:
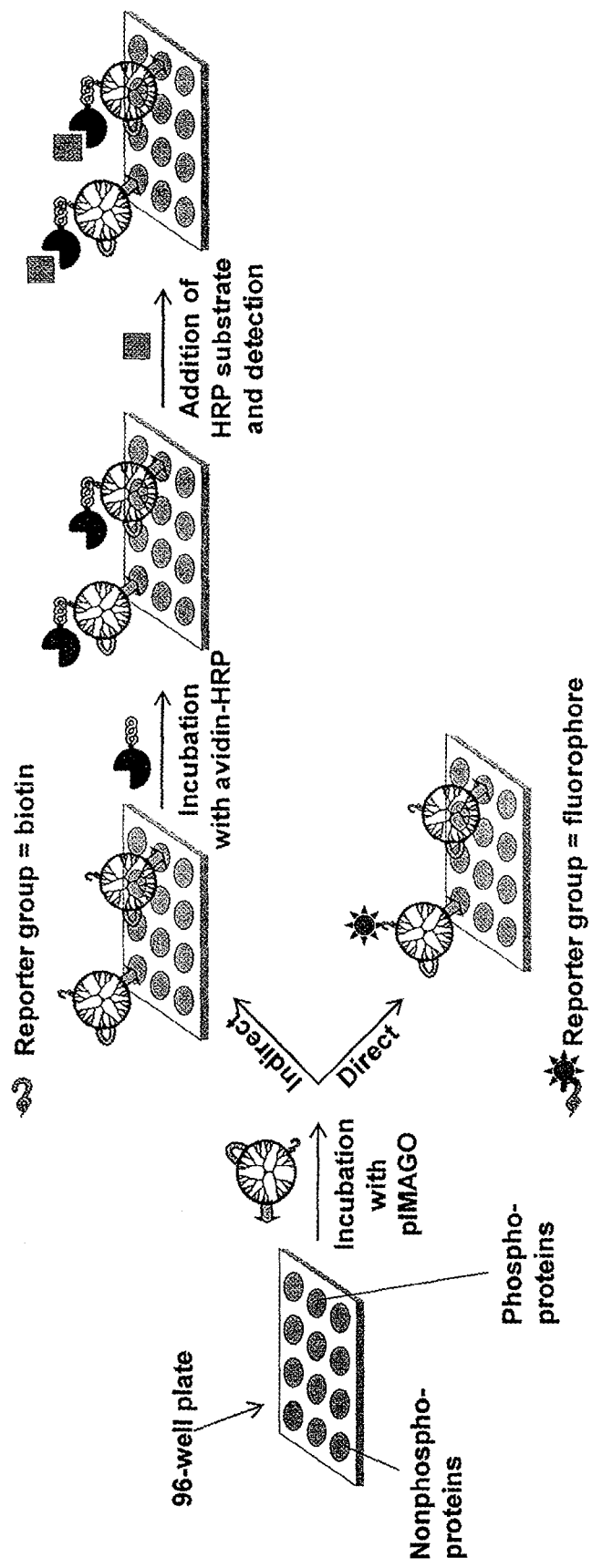
FIG. 11. Scheme illustrating steps in assaying for phosphorylated proteins in a 96 well plate using pIMAGO and either indirect using avidin-HRP (upper branch) or direct fluorophore (lower branch) detection.

Referring now to FIG. 11, this figure is a schematic representation of experimental workflow for pIMAGO-based phosphoprotein detection in a 96-well plate format. After the phosphoproteins of interest are bound to the wells, the wells can be briefly incubated with the pIMAGO reagent, which selectively binds to phosphate groups. For direct assay, signal is detected directly using a spectrophotometer. For indirect assay, linked enzyme, such as HRP-linked avidin, is then added into the wells, exclusively attaching to the biotin groups of pIMAGO. Finally, a colorimetric or chemiluminescent HRP substrate is incubated with the wells to enable signal detection.

Figure 12:
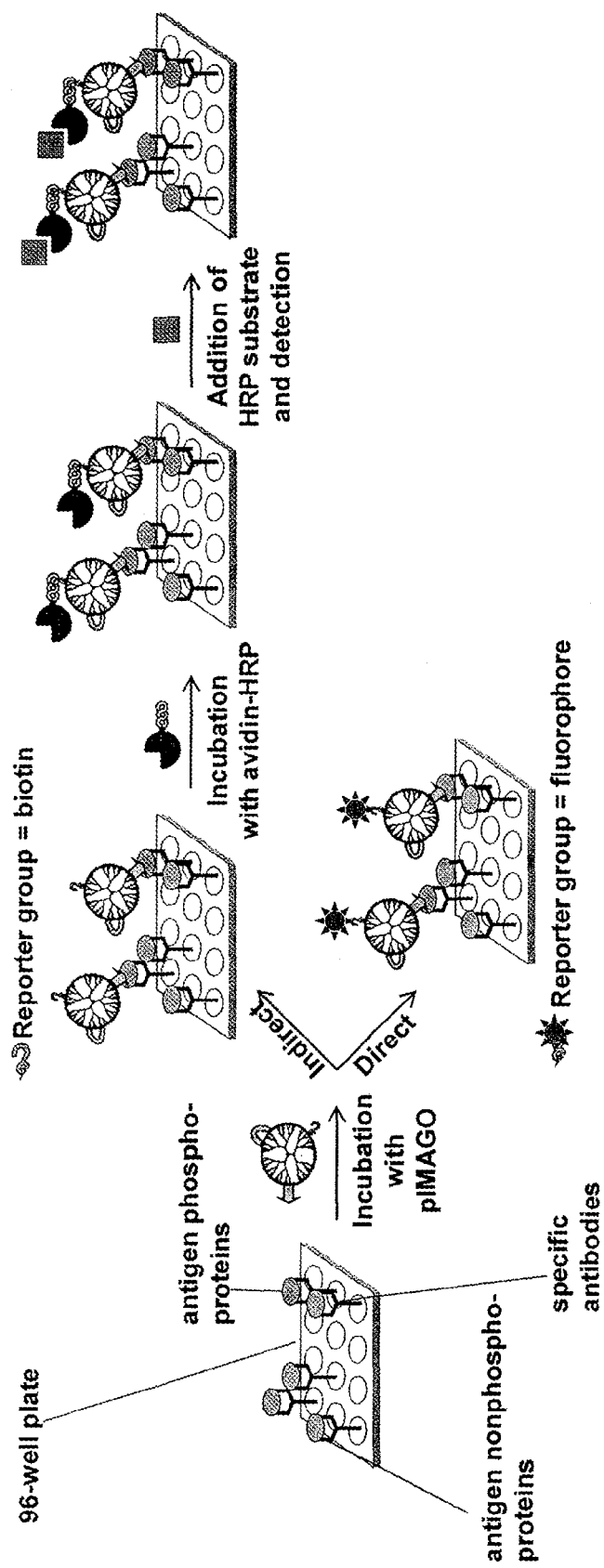
FIG. 12. Scheme illustrating steps in assaying for proteins immobilized using antibodies in a 96 well plate using pIMAGO either indirectly using avidin-HRP (upper branch) or directly using a fluorophore (lower branch) detection.

Referring now to FIG. 12, this figure is a schematic representation of experimental workflow for pIMAGO-based phosphoprotein detection in a sandwich 96-well plate format. In the first step, a specific antibody is bound to the well passively and proteins of interest are bound to the wells through their antibodies. The rest of procedure is the same as in FIG. 11.

Figure 13:
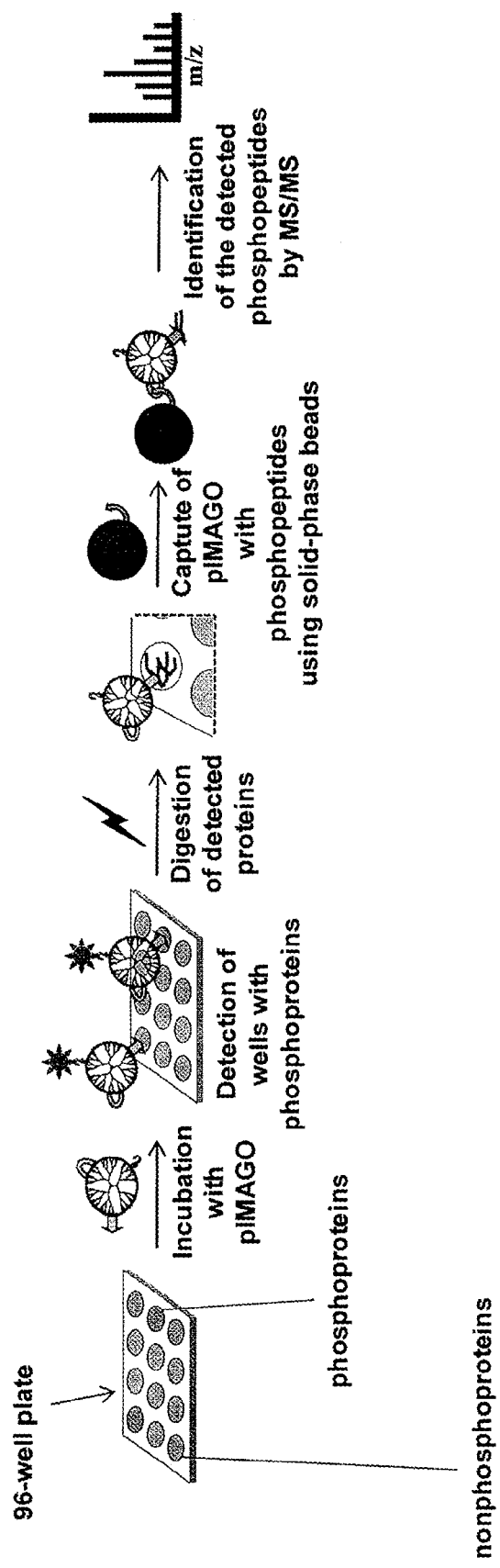
FIG. 13. Scheme illustrating steps in assaying for phosphorylated proteins in a 96 well plate using an in situ digestion of proteins and mass spectrometry.

Referring now to FIG. 13, this figure is a schematic representation of experimental workflow for pIMAGO-based phosphoprotein detection in a 96-well plate format followed by mass spectrometric analysis. After ELISA analysis, phosphoproteins are digested with a protease and solid phase beads are added to the well to capture pIMAGO and its bound phosphopeptides. In the final step, phosphopeptides are recovered and analyzed by mass spectrometric analyses.

Upon selection of suitable standards, this method can be used to determine the phosphorylation state of a phosphoprotein. After creating a standard curve of the measured signal it is possible determine the absolute amount of phosphorylated protein present in a sample.

These inventive reagents can be used in high throughput screening for kinase inhibitors. This approach is particularly useful if there are no phospho-site specific antibodies available or is the antibodies available are scarce and/or expensive.

EXPERIMENTAL

Materials and Methods

All reagents for pIMAGO synthesis, protein dephosphorylation, Syk inhibitor, and all standard proteins were obtained from Sigma-Aldrich. SnakeSkin dialysis tubing, HRP substrates, SuperBlock T20 blocking buffer, and 96-well plates were bought from Pierce. The plate reader was obtained from Biotek, and centrifugal filter units from Millipore. Purified Acm1 was generously provided in phosphorylated and unphosphorylated forms by the Hall group (Purdue University).

1. Synthesis of Phosphorylation Detect No Reagents Suitable for Blotting and Imaging on Membrane.

Dried 200 µl of PAMAM (polyamidoamine) dendrimer generation 4 solution (provided as 10% (wt/vol) in methanol; Sigma-Aldrich) in a microfuge tube. Resolubilized dried dendrimer in 3 ml of 150 mM MES buffer in water (2-(N-morpholino)ethanesulfonic acid; pH 5.5) and transferred into a 10-ml round-bottom flask with a magnetic stir bar. Added 6.5 mg of 2-carboxyethyl-phosphonic acid, 10 mg of N-hydroxysuccinimide (dissolved in 100 µl water), and 100 mg EDC (1-ethyl-3-(3-dimethylaminopropyl) carbodiimide hydrochloride) into the flask and stirred overnight to functionalize the dendrimer with phosphonic acid. Next day, added 1 mL of 150 mM MES (pH 5.5), 20 uL of glyceric acid, 16 mg NHS, 150 mg EDC, and stirred overnight. Dialyzed the solution against water for 7-8 hours to overnight using Snakeskin® pleated dialysis tubing (3,500 MWCO, 22 mm dry diameter, Pierce) to remove any remaining unreacted reagents (replaced water periodically). At this point, the mixture was collected and stored at 4° C. One-third of the reagent solution was dried down to 1 mL using SpeedVac concentrator (Savant). Next, 40 mg of sodium (meta)periodate was added to the solution and incubated for 40 min with agitation in the dark at room temperature which was used for biotin conjugation. The mixture was dialyzed overnight against water. The reagent solution was transferred into a microfuge tube, 20 ug of biotin-hydrazide was added in and incubated overnight at room temperature with agitation to functionalize Phos-blot with biotin. The reagent was dialized overnight again and dried down to 1 mL. Finally, 20 uL titanium oxychloride stock in 30% HCl was added in, and incubated for 1 hour with agitation at room temperature to chelate titanium with phosphonic acid groups on the dendrimer. The solution was lastly dialyzed against 0.01% HCl overnight to remove any unbound titanium. The finished PolyMAC-Ti product was mixed with 20 uL of 1M HCl and stored at 4° C.

2. Synthesis of a Low Molecular Weight Phosphoprotein Detecting Reagent Suitable for In-Gel Probing of Proteins.

The synthesis of small molecule weight pIMAGO reagents is based on a standard solid phase synthesis approach. It started with propylamine-PEG resin, followed by the following coupling steps consecutively: 1) acid-cleavable linker; 2) Fmoc-Lys(Biotin)-OH; 3) remove the Fmoc group and couple FITC; 4) 2-carboxyethyl-phosphonic acid; and 5) titanium oxychloride. Finally, the reagents were cleaved off the solid phase with 95% TFA.

3. Cell Culture and Protein Dephosphorylation.

HeLa cells were grown to confluency in DMEM media supplemented with FBS, 1% sodium pyruvate and 0.5% streptomycin/penicillin. The cell were trypsinazed, collected and lysed in 1 mL of lysis solution (50 mM Tris-HCl, pH 7.5, 150 mM NaCl, 5 mM EDTA, 1% NP-40, 1 mM sodium orthovanadate, 1× phosphatase inhibitor cocktail (Sigma), 10 mM sodium fluoride) for 20 minutes on ice. For the sample to be phosphatase-treated, all the phosphatase inhibitors (i.e., phosphatase inhibitor cocktail, sodium fluoride and sodium orthovanadate) were omitted. The cell debris was cleared at 16,100×g for 10 minutes, and supernatant containing soluble proteins collected. The concentration of the cell lysate was determined using the BCA assay.

In order to dephosphorylate proteins in the lysate, the 50 ug sample was incubated with 10 units of calf intestine alkaline phosphatase in 1×CIAP buffer for 30 min at 37° C. To stop the enzyme activity, the sample was boiled for 5 min in 1×LDS sample buffer.

4. Running Gels and Detections Phosphorylated Proteins.

Protein samples were boiled in 1×LDS sample buffer and 20 mM DTT and loaded on 12% polyacrylamide gel. The gel was run at 150 V constant voltage for 90 min in 1×MOPS buffer. The proteins were then transferred onto a PVDF membrane in 1× NuPAGE transfer buffer with 15% methanol for 65 min at 275 mA at constant current. The membrane was blocked by rocking for 1 hr with 10 mL of 1% BSA in 1×TBST, rinsed with water and incubated by rocking with 20 uL of Phos-blot reagent in 10 mL of 100 mM glycolic acid/1% TFA solution. The blot was washed four times with the 100 mM glycolic acid/1% TFA solution and three times with 1×TBST. For detection, the membrane was incubated with 1:5,000 dilution of avidin-peroxidase in 1×TBST containing 1% BSA for 40 min while rocking. The membrane was lastly washed four times with 1×TBST and detected with ECL detection solution.

5. pIMAGO-Based Detection of Phosphoproteins in a 96-Well Plate.

The standard proteins, α-casein, β-casein, BSA, Acm1, and Syk, were adsorbed onto a polystyrene 96-well plate by incubating each well with different amounts of the proteins in 100 uL of carbonate buffer, pH 9.6, overnight at 4° C. The protein solution was then removed and the wells were blocked for 2 hours with 200 uL of SuperBlock T20 blocking buffer (Thermo) supplemented with 1% BSA. Successively, each well was incubated with 500 mL of the pIMAGO reagent in 100 uL of 500 mM glycolic acid/1% trifluoroacetic acid solution for 1 hour. The wells were washed 4 times with the 500 mM glycolic acid/1% trifluoroacetic acid solution, twice with the SuperBlock T20 blocking buffer, and blocked again for 2 hours with the SuperBlock T20 blocking buffer containing 1% BSA. Finally, the wells were incubated for 1 hour with 100 uL of the 1:2,000 dilution of avidin-HRP in SuperBlock T20 blocking buffer containing 1% BSA. After washing, 100 uL of the HRP sunstrate was added (either for colorimetric or chemiluminescent detection) and the plate was incubated for 2-3 minutes to allow for the signal to develop. For colorimetric assays, further signal development was stopped by addition of 150 uL of 2% oxalic acid. The plate was then read with the plate reader (Biotek) using either 415 nm wavelength or the luminescence detection method. The phosphoprotein signal was compared to and subtracted from any background signal produced by nonphosphorylated proteins (i.e., BSA or unphosphorylated Acm1), which were usually used at higher amounts to eliminate any potential false positives.

6. Syk Autophosphorylation and Inhibition Assay.

Purified Syk protein was adsorbed onto a number of wells in a polystyrene 96-well plate by incubating each well with 50 ng of the protein in 100 uL of carbonate buffer, pH 9.6, overnight at 4° C. The wells were blocked for 2 hours with 200 uL of SuperBlock T20 blocking buffer (Thermo) supplemented with 1% BSA. At this point, each well (except the first control) was incubated with 2 uL of Calf Intestine Alkaline Phosphatase (CIAP) in 1×CIAP buffer at 30° C. to remove most of the residual phosphorylation on Syk. The wells were washed and incubated with 500 uM ATP and 1 mM $MnCl_2$ in 30 mM HEPES (pH 7.5) buffer for 1 hour at 30° C. Where specified, Syk inhibitor piceatannol was added along with the ATP at different concentrations (10 ug/mL, 20 ug/mL, 100 ug/mL) to prevent autophosphorylation. After washing the wells, the pIMAGO binding steps was carried out as already described herein.

7. Design of pIMAGO Reagents and Procedures for Phospho-Detection on Membrane.

The specific detection of phosphorylation in gel, on membrane, or directly in cells has remained elusive. The compound PolyMAC, comprising a soluble nanopolymer functionalized with moieties that include titanium can selectively enrich phosphopeptides from a very complex mixture. One component of PolyMAC is a soluble polyamidoamine synthetic nanopolymer (e.g., dendrimer), which has a hyper-branched surface that can be functionalized with desired chemical groups. Besides solubility, the advantages of using dendrimers include high structural and chemical homogeneity, compact spherical shape, and controlled surface functionalities. U. Boas and P. M. Heegaard, Dendrimers in drug research *Chem Soc Rev* 33 (1), 43 (2004). The homogeneous and hyper-branched nature of the reagent exhibited superior specificity for phosphopeptides, unparallel high recovery and fast binding kinetics. Continuing work in this area resulting in the development of new reagents and strategies for phosphorylation detection, referred to herein as pIMAGO reagents (FIG. 3). This reagent, similar to PolyMAC, is based on a soluble nanopolymer such as polyamidoamine (PAMAM) derivatized with two types of functional groups, a reactive group that binds to phosphorylated molecules specifically, and a reporter group for direct or indirect by spectroscopic detection.

Referring now to FIG. 4, a specific example is illustrated in FIG. 4B, in which the binding group is titanium (IV) and the reporter is biotin. The high ratio of reporter to binding groups facilitates the highly sensitive detection. Referring now to FIG. 5, a typical Western blotting procedure using this reagent for selective blotting of phosphorylated proteins is illustrated. Proteins, including phosphorylated and non-phosphorylated proteins, are separated on SDS-PAGE. After transferring proteins onto a PVDF membrane, the detection procedure closely resembles Western blot protocol, where the membrane is blocked with BSA in TBST buffer, incubated with the pIMAGO reagent for 1 hr in place of a primary antibody, and followed by the incubation with avidin-horseradish peroxidase instead of a secondary antibody. In the final step, phosphoproteins are detected by chemiluminescence.

A faster detection approach can be utilized if the biotin groups are replaced with a fluorophore (e.g. fluorescein isothiocyanate (FITC)), thus enabling immediate detection with a regular image scanner after the blotting (FIG. 5B). Two procedures can be used separately or in parallel depending on the nature of the application.

8. Direct In-Gel Detection of Phosphor-Molecules with pIMAGO Reagents.

Figure 4C:
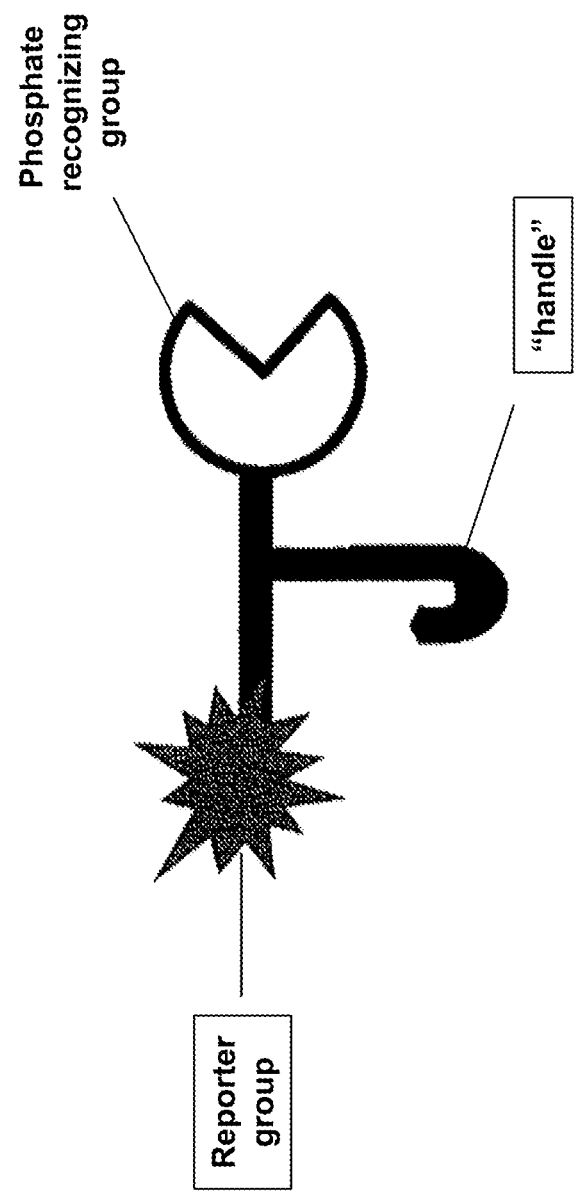
FIG. 4C. Illustration of a low molecular weight reagent for detecting phosphorylated groups. The reagent includes a reporter, a phosphate binding group and 'handle' for attaching the reagent to a surface.
Figure 4D:
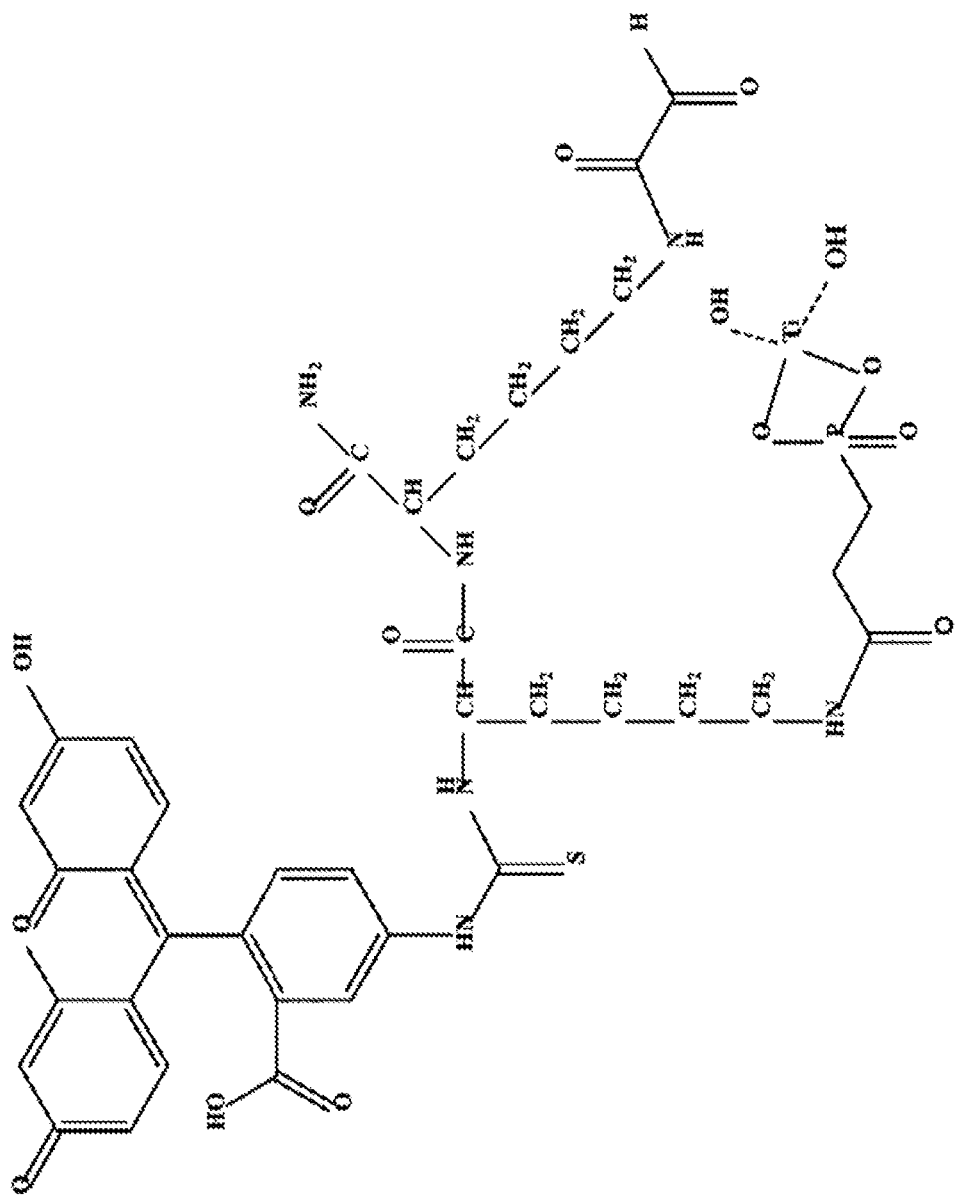
FIG. 4D. Illustration of an example of a small reagent for detecting phosphorylated groups. The reagent that includes a reporter, a phosphate binding group and 'handle' for attaching the reagent to a surface.

Direct in-gel detection of phosphorylated molecules (i.e., proteins or nucleic acids) is extremely appealing, because the transferring step is not always efficient for certain proteins and the procedure is tedious. In order to facilitate this approach a small molecule-based reagent comprising a reporter group (dye or fluorescence tag) and immobilized titanium was made (FIG. 4A). One embodiment of this type of reagent is illustrated in FIG. 4B. In still another embodiment the basic reagent was modified to include a handle group in the molecule (FIGS. 4C, and 4D). This lower less bulky reagent is well suited for direct in-gel staining. It is also compatible with assays that call for follow-up in-gel digestion and perhaps mass spectrometry analysis for the identification of phosphoproteins and phosphorylation sites. The small size of the reagent assures easy access to the proteins or nucleic acids for enzymes that process the gel bound sample and fast removal from the gel after staining is complete. Once identified the band that includes the phosphoprotein protein can be removed from the gel, digested. Phosphopeptides labeled with the reagent can isolated using the handle group, followed by mass spectrometry analysis for protein identification and phospho-site localization.

9. Specific Visualization of Phosphorylated Proteins on a Blotting Membrane.

Figure 7:
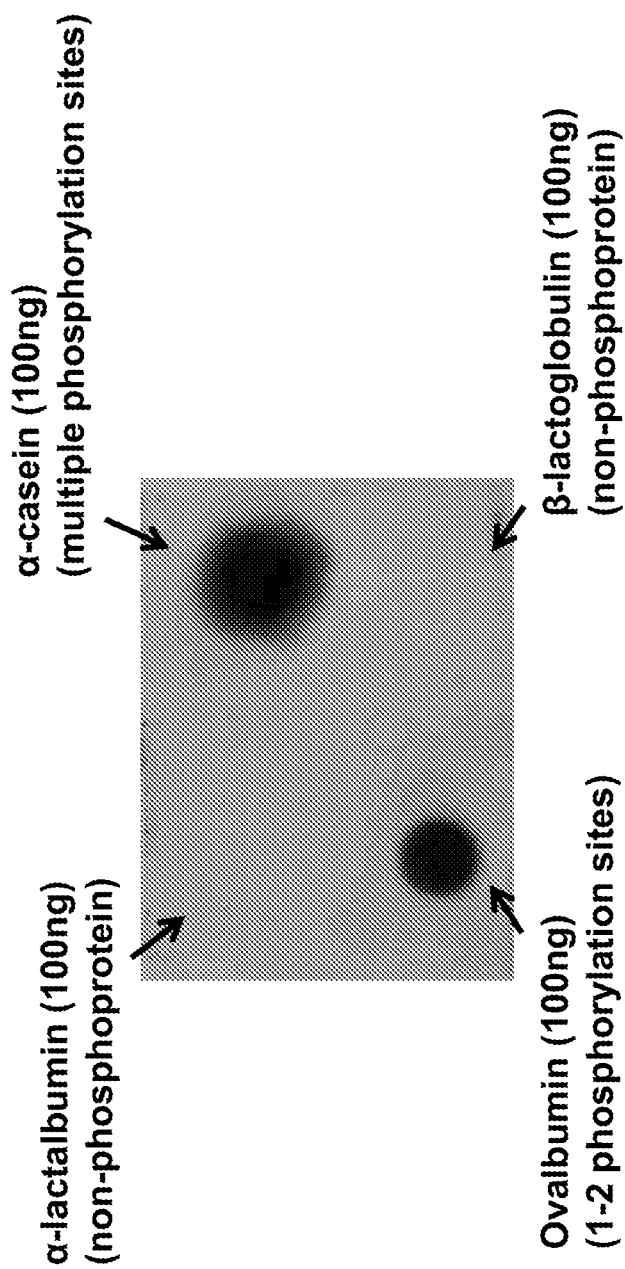
FIG. 7. Analysis of 4 proteins using a dot blot analysis and probing with pIMAGO.
Figure 8:
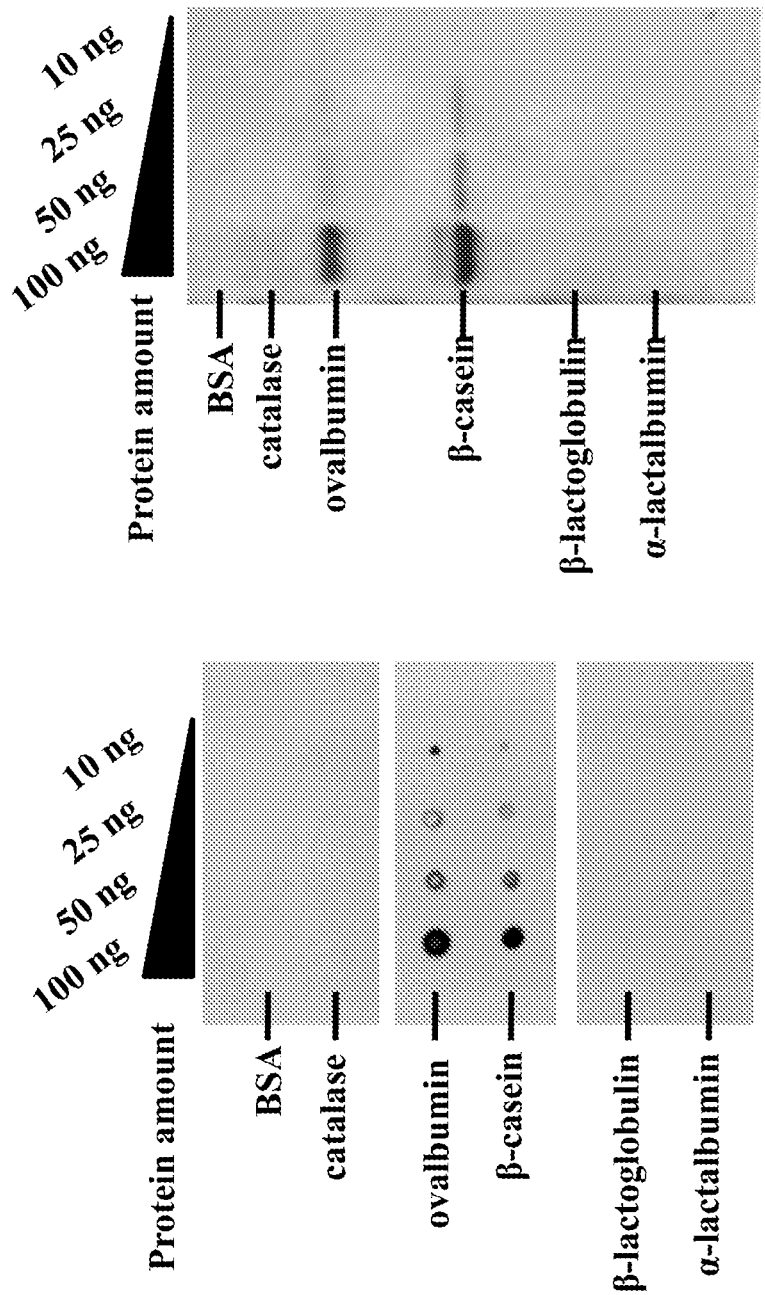
FIG. 8A. Analysis of 6 proteins loaded at different amounts using a dot blot analysis and probing with pIMAGO.
FIG. 8B. Analysis of 6 proteins loaded at different amounts using a Western blot-type analysis probed with phosphorylation imaging reagents made in conformity with the disclosure.
Figure 9:
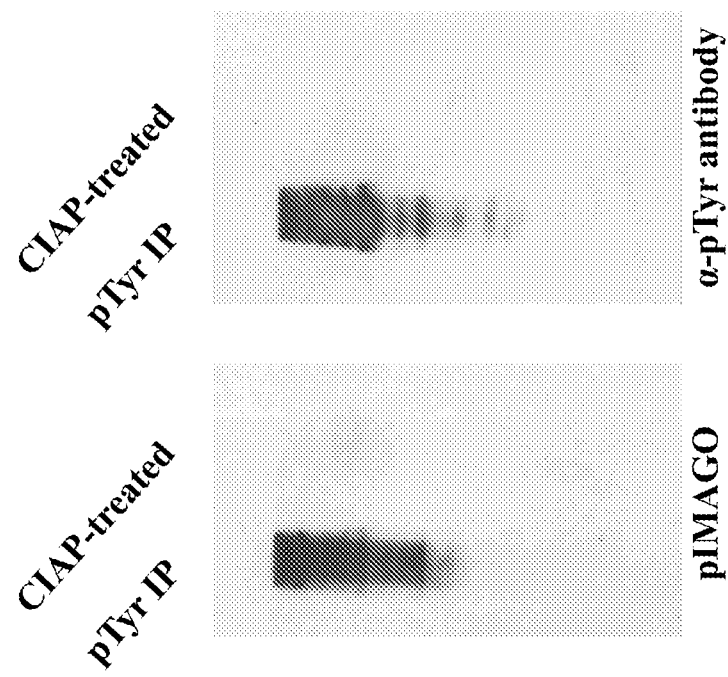
FIG. 9. Western blot of tyrosine rich protein performed using pIMAGO reagent (left) and anti-phosphotyrosine (pTyr) antibody (right). A lane in each experiment includes pTyr-IP treated with calf intestine alkaline phosphatase (CIAP) was also analyzed.
Figure 10A:
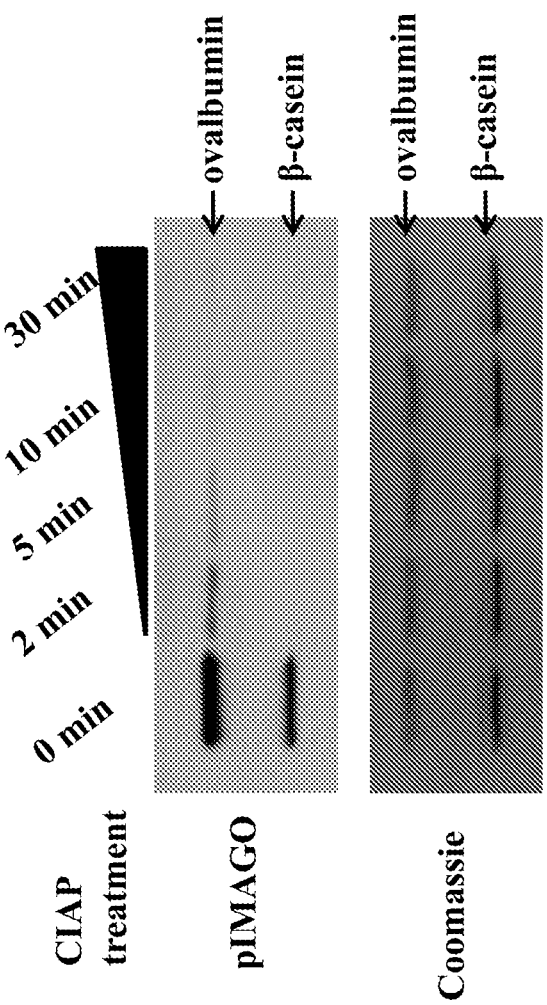
FIG. 10A. Analysis of ovalbumin or alpha-casein treated for different periods of time with CIAP and stained with coomassie blue (bottom) or probed with pIMAGO (top).
Figure 10B:
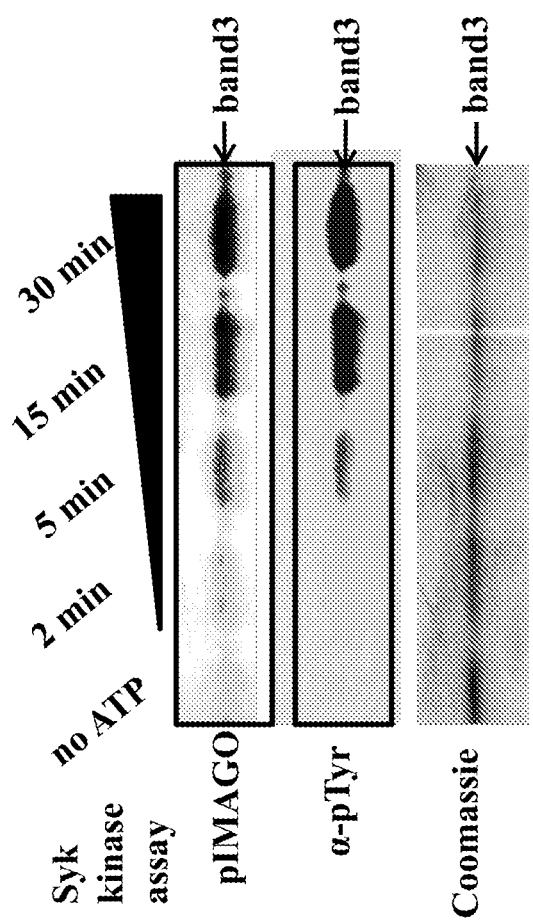
FIG. 10B. Results of an in vitro kinase assay of band 3 for different periods of time with Syk kinase; stained with coomassie blue dye (bottom), or probed with pY antibody (middle) or pIMAGO (top).
Figure 10C:
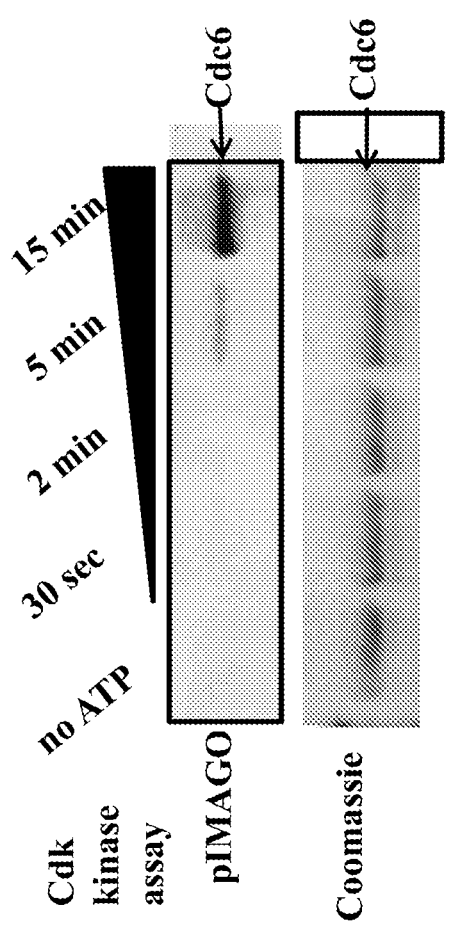
FIG. 10C. Analysis of in vitro kinase assay of Cdc6 phosphorylation by Cdk1. These blots were either stained with coomassie blue (bottom) or probed with pIMAGO.

In order to visualize phosphorylated proteins, phospho-imaging reagents that included biotin were made and used in Western blotting analysis. In these test, the phosphorylated proteins, α-casein and ovalbumin, and two nonphosphoproteins, BSA and β-lactoglobulin, were spotted on a PVDF membrane. Referring now to FIG. 7, only phosphoproteins were specifically detected at nanogram levels using the ECL system. No ECL signal was detected on the spots of the nonphosphorylated proteins. In the absence of a reagent that includes a metal such as titanium and that binds phosphorylated molecules (i.e., using a similar reagent except missing titanium), no ECL signals were detected on the spots of phosphorylated proteins (data not shown).

10. Visualization of Various Phosphorylated Proteins on a Blotting Membrane.

Figure 14:
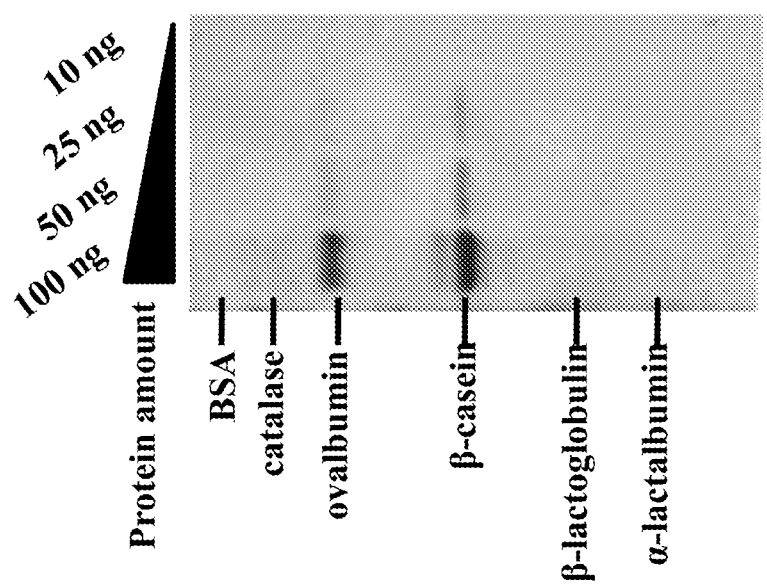
FIG. 14. Blot including both phosphorylated and non-phosphorylated proteins probed with pIMAGO.

Referring now to FIG. 14, a pIMAGO reagent was used in an electroblotting analysis carried out after SDS-PAGE. The proteins, including two phosphorylated proteins (alpha-casein and ovalbumin) and four unphosphorylated proteins (BSA, catalase, alpha-lactalbumin and beta-lactoglobulin), were mixed together at equivalent ratios and at different amounts, ranging from about 100 ng to about 10 ng each. Still referring to FIG. 14, these results demonstrate good selectivity and sensitivity of the blotting reagent, allowing detection of only alpha-casein and ovalbumin at the protein amounts of close to 10 ng.

11. Determining the Phosphorylation State of DG75 Cells.

Figure 15:
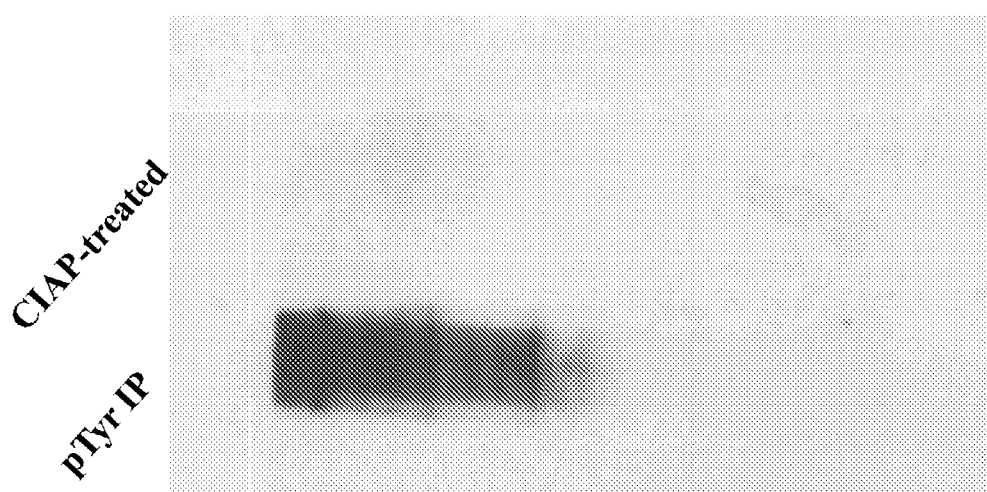
FIG. 15. Blot including both phosphorylated and non-phosphorylated proteins probed with pIMAGO.

Referring now to FIG. 15, in order to determine if the reagents are applicable for complex samples, phosphate-specific detection was used to analysis the tyrosine phosphorylation status of DG75 cells. It has been well established that tyrosine phosphoproteins can be immune-purified with relatively high specificity. With an anti-tyrosine phosphorylation antibody (PT66), we enriched tyrosine phosphoproteins. Then half of enriched samples were treated with a general calf intestine phosphatase (CIAP) for dephosphorylation. Samples were run on the SDS-PAGE gel, transferred, and blotted with pIMAGO reagent. The results show a significant decrease in signal from the phosphatase-treated sample compared to the control lane. The signal was still slightly detectable in the phosphatase-treated lane likely is due to incomplete dephosphorylation of all phosphoproteins in the sample.

It is demonstrated that a reagent, referred to as PolyMAC, and consisting of a soluble nanopolymer functionalized with titanium can selectively enrich phosphopeptides from a very complex mixture. One component of PolyMAC is a soluble polyamidoamine synthetic nanopolymer (e.g. dendrimer) with a hyperbranched surface that can be functionalized with desired chemical groups. The advantages of using a dendrimer include outstanding solubility, high structural and chemical homogeneity, compact spherical shape, and controlled surface functionalities. The homogeneous and hyper-branched nature of the reagent exhibited superior specificity for phosphopeptides, unparallel high recovery and fast binding kinetics.

This reagent was used, with a few modifications, for the selective detection of phosphorylated proteins bound to a 96-well plate in ELISA format. In these exemplary assays the reagent, termed pIMAGO one form of a pIMAGO reagent is shown in FIG. 2. Referring to FIG. 2, the linker core comprising a dendrimer was functionalized with 10-15 Ti groups, enabling strong and selective binding to the phosphoproteins; as well as 15-20 biotin molecules, which can bind to enzyme-labeled avidin for superior detection sensitivity. Here, each dendrimer bound to a phosphosite will enhance the signal by more than 10-fold, allowing for excellent detection of low abundant proteins (pIMAGO-ELISA workflow is outlined in FIGS. 11, 12 and 13).

Figure 16A:
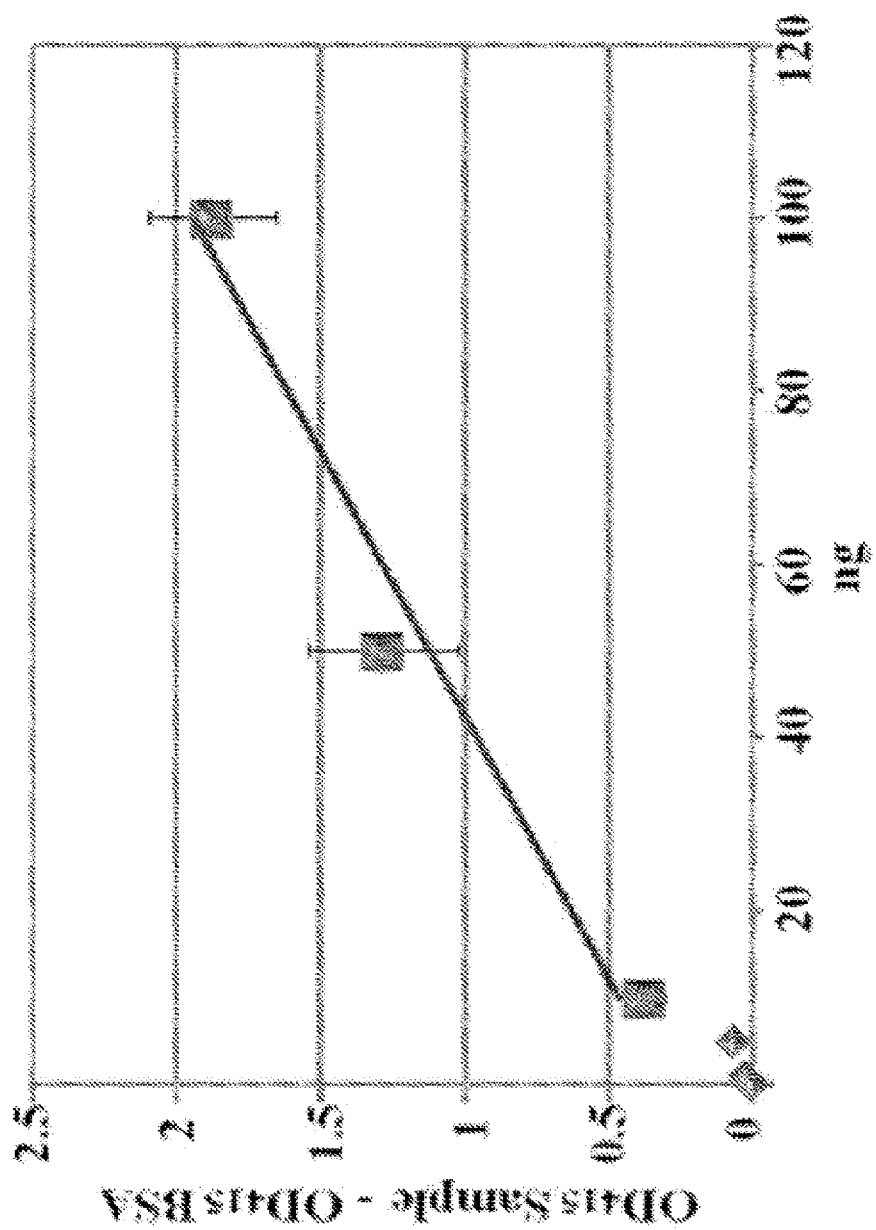
FIG. 16A. Quantitative analysis of α-casein probed with pIMAGO.
Figure 16B:
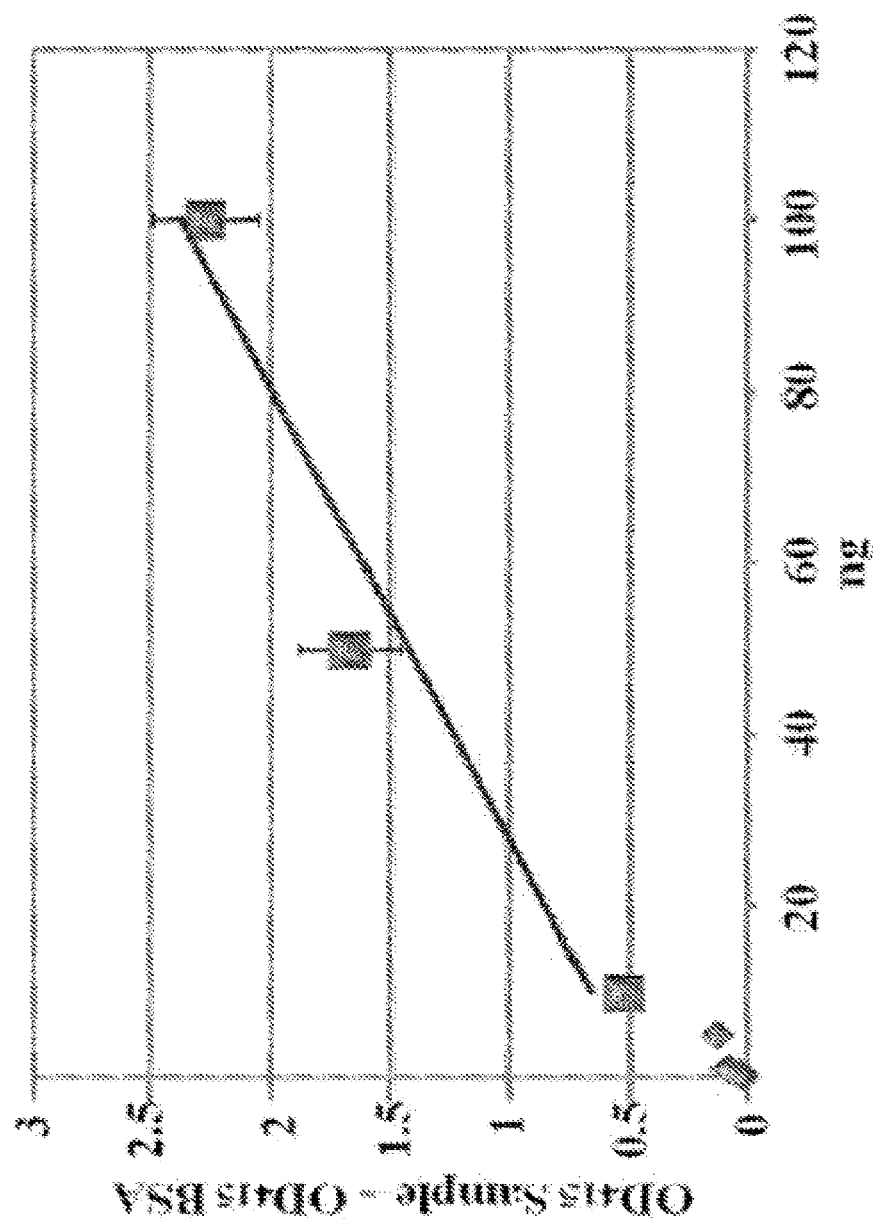
FIG. 16B. Quantitative analysis of β-casein probed with pIMAGO.
Figure 16C:
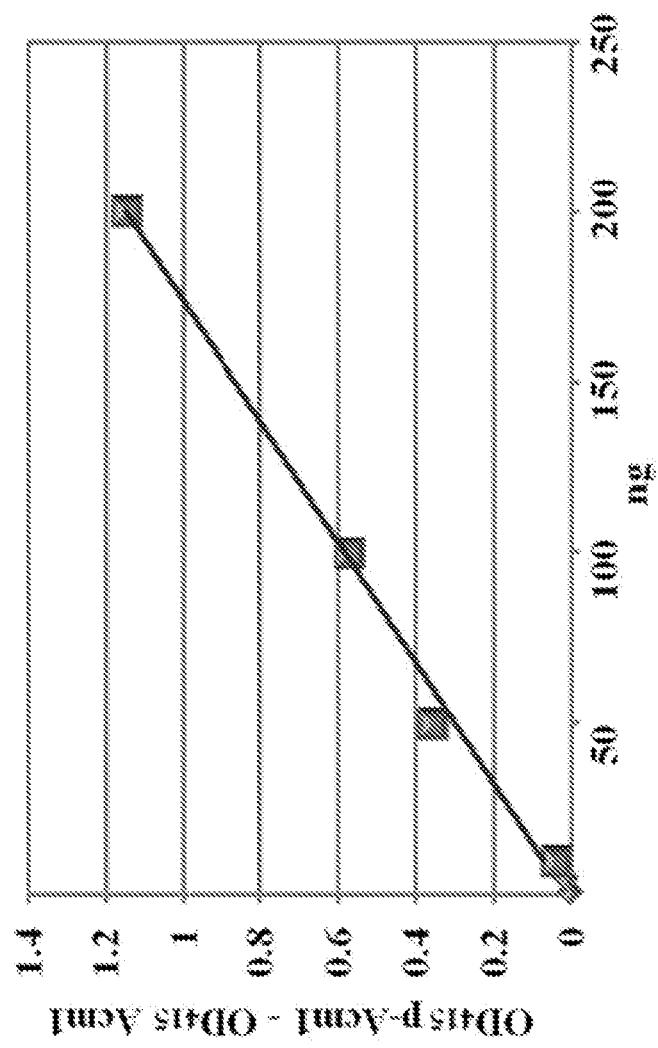
FIG. 16C. Quantitative analysis of phospho-Acm1 probed with pIMAGO.
Figure 16D:
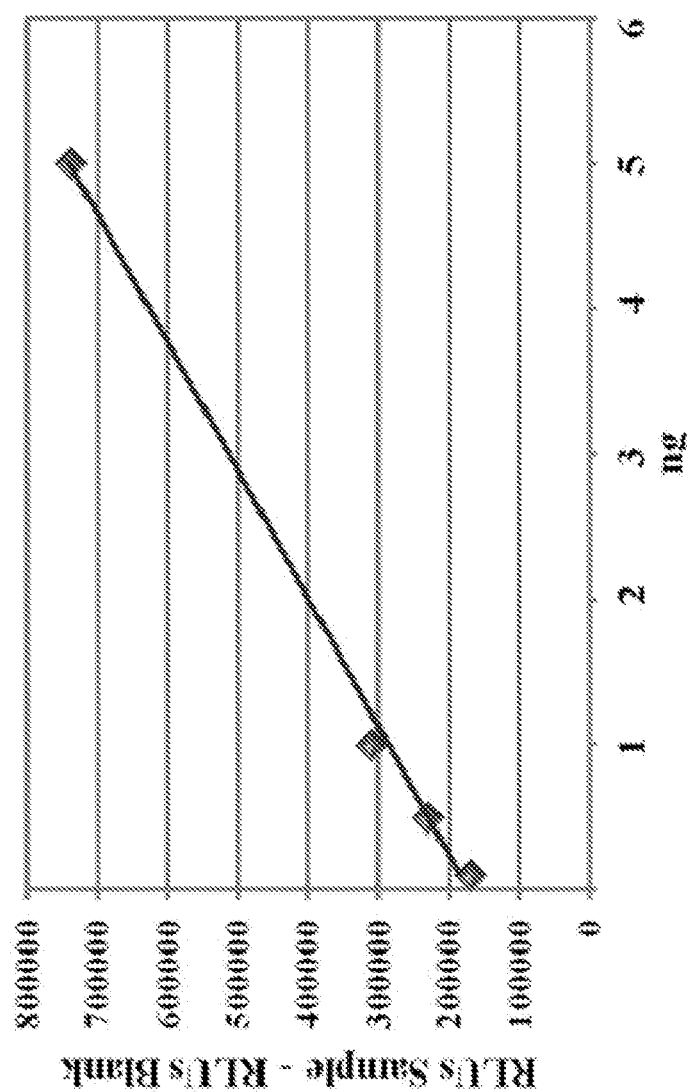
FIG. 16D. Quantitative analysis of a β-casein blot probed with pIMAGO using a chemiluminescent reporter.

The practicality of the new reagent was demonstrated on a number of standard phosphoproteins bound to the plate at different amounts. Some of these assays used α-casein, β-casein, and phospho-Acm1 as our phosphoproteins; and BSA and unphosphorylated Acm1 as the background controls. The colorimetric assay conditions demonstrated quantitative capabilities of the approach, as well as high sensitivity, with signal-to-noise ratio allowing for the detection of 1 ng of a phosphoprotein. Quantitative capabilities were achieved using 10 ng of each phosphoprotein, representing biologically relevant protein concentrations (see for example FIGS. 16A-C). If more sensitivity is required pIMAGO can be modified to detect and quantify phosphoproteins at about the 100 pg level by replacing a colorimetric-based detection system with a chemiluminescent detection system (see for example FIG. 16D). Lehel, C., Daniel-Issakani, S., Brasseur, M, and Strulovici, B. (1997) A chemiluminescent microtiter plate assay for sensitive detection of protein kinase activity, *Analytical biochemistry*. 244, 340-346. Similarly, a nanopolymer can be synthesized with a fluorescent group instead of biotin, offering an easy and sensitive direct ELISA procedure. Babcook, J., Watts, J., Aebersold, R., and Ziltener, H. J. (1991) Automated nonisotopic assay for protein-tyrosine kinase and protein-tyrosine phosphatase activities, *Analytical biochemistry*. 196, 245-251.

In order to demonstrate the capacity of pIMAGO for inhibitor screening, purified Spleen tyrosine kinase (Syk) was immobilized in the wells of to a 96-well plate. Syk was dephosphorylated in a number of wells. Next, ATP and MnCl$_2$ were introduced into the wells to promote its autophosphorylation. In the specified assays, piceatannol, a Syk inhibitor, was added along with the ATP at different concentrations. Oliver, J. M., Burg, D. L., Wilson, B. S., McLaughlin, J. L., and Geahlen, R. L. (1994) Inhibition of mast cell Fc epsilon R1-mediated signaling and effector function by the Syk-selective inhibitor, piceatannol, *J Biol Chem*. 269, 29697-29703. The signal was subtracted from the background of BSA that was also incubated with ATP and MnCl$_2$ to eliminate any false positive signal due to bound ATP (in our case, we did not see any increase in BSA signal after incubation with ATP; data not shown).

Figure 17:
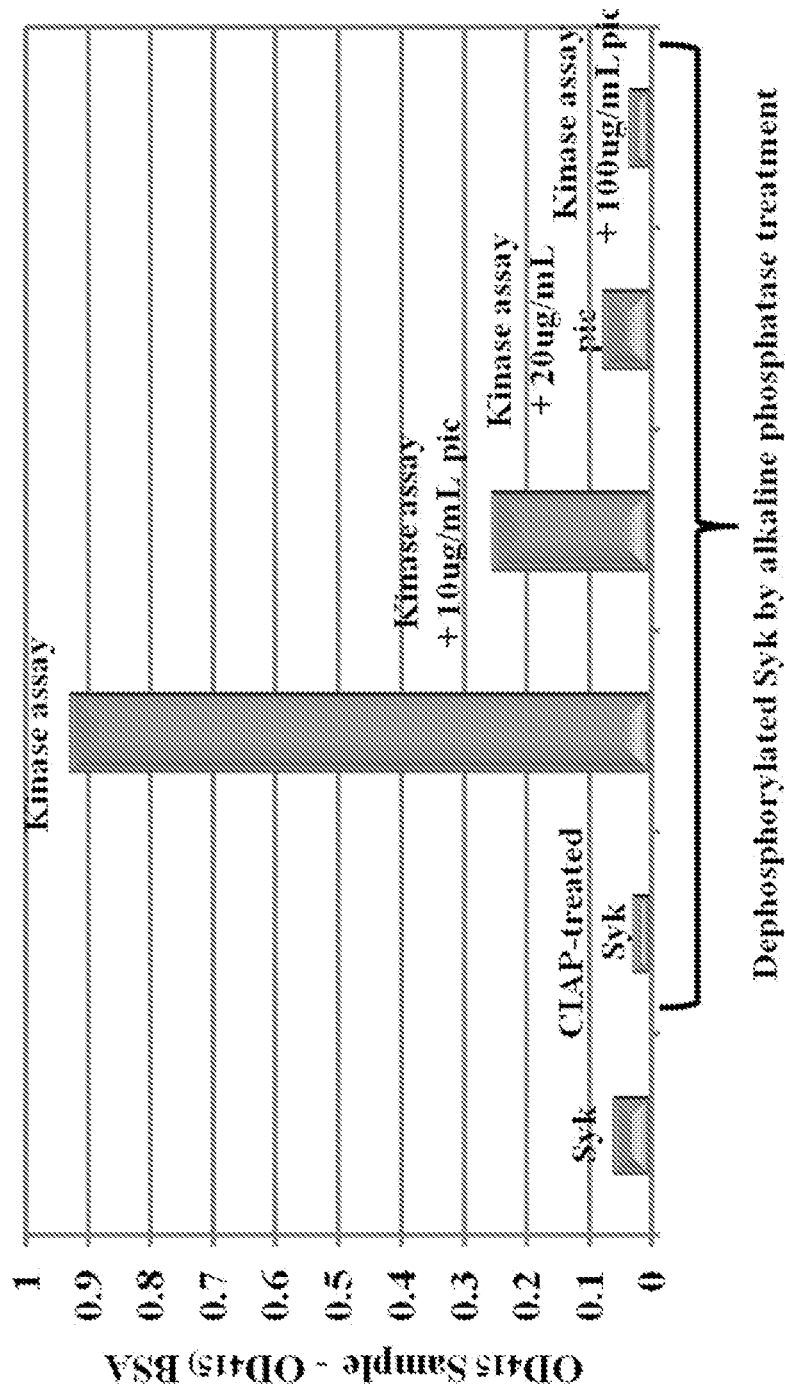
FIG. 17. Bar graph illustrating the ability of pIMAGO to detect kinase activity a 96 well plates.
Figure 18:
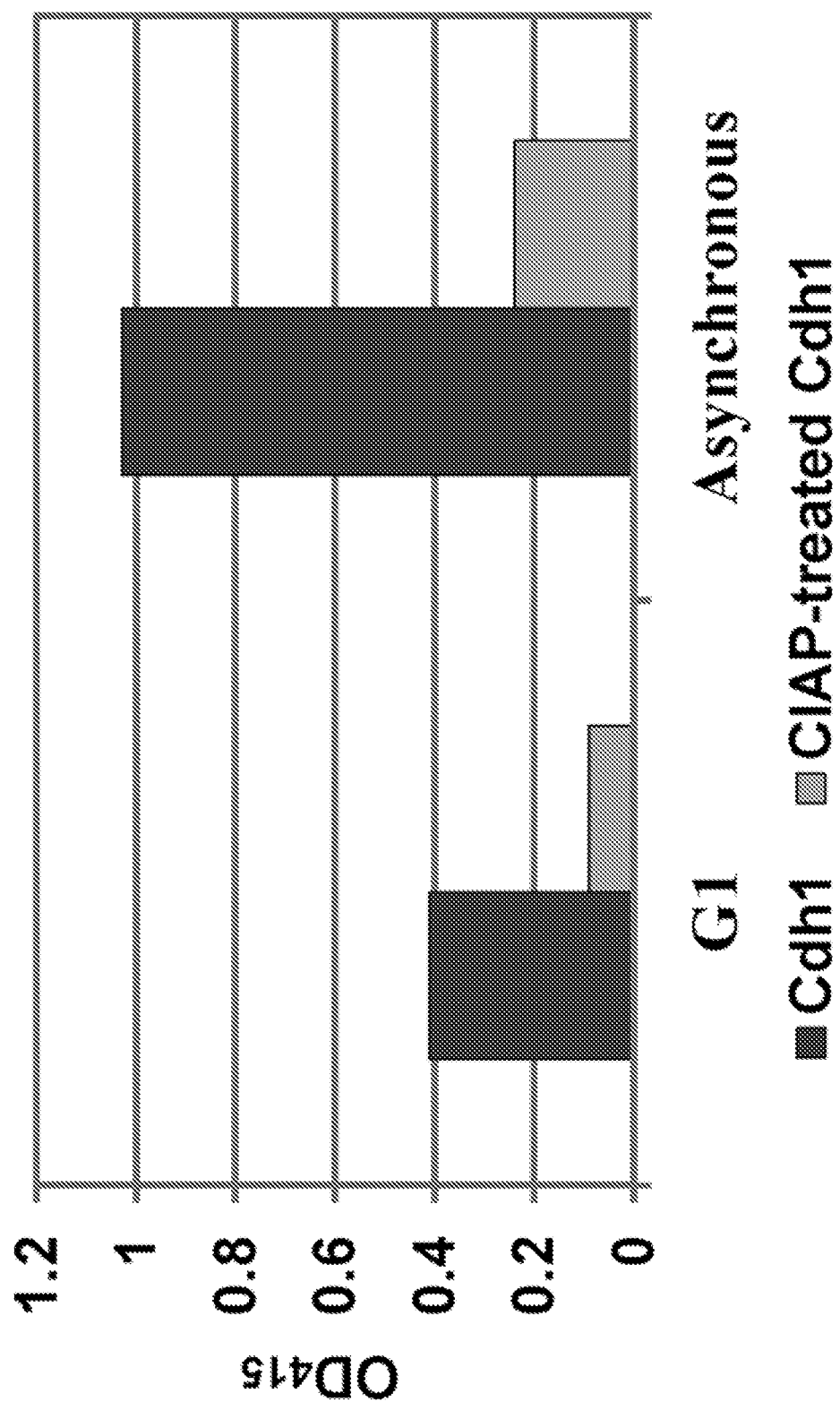
FIG. 18. Bar graph illustrating the difference in phosphorylation state of Cdh1 measured using pIMAGO and a 96 well plate in cells in G1 phase or during asynchronous growth.

The results are summarized in FIG. 17. pIMAGO-based testing of Syk autophosphorylation and inhibition by piceatannol. 50 ng of purified active Syk kinase was bound to the wells, dephosphorylated, and then allowed to undergo autophosphorylation through the addition of ATP and MnCl$_2$. In the designated cases, different amounts of Syk inhibitor piceatannol were added during the kinase assay to inhibit autophosphorylation. The signal was subtracted from 100 ng BSA background.

Still referring to FIG. 17, these results demonstrate that the pIMAGO-based detection signal was reduced after dephosphorylation to almost the background level, and then greatly increased after the in vitro kinase assay. However, the signal increase was not as dramatic after piceatannol was introduced into the assay. This is particularly true during the use of the potent 100 ug/mL piceatannol concentration, where the signal remained at the level of the dephosphorylated Syk. These results demonstrated the capability of pIMAGO for determining changes in kinase activity, thereby demonstrating that pIMAGO can be used simultaneously assay for a range kinases and a kinase inhibitors.

Reagents such as pIMAGO have broad utility in uses such a the ELISA procedures disclosed herein for both qualitative and quantitative assessment of protein phosphorylation. These pIMAGO reagents provide high-through put sensitive methods for a variety of analyses, including, but not limited to, phosphorylation stoichiometry assays, and screening for kinase inhibitors. It has the potential to become a single-reagent procedure for any phospho-ELISA studies, replacing the numerous costly phosphosite specific antibodies.

12. Micro Titer Plate Based Assay for Phosphorylated Molecules.

Figure 20:
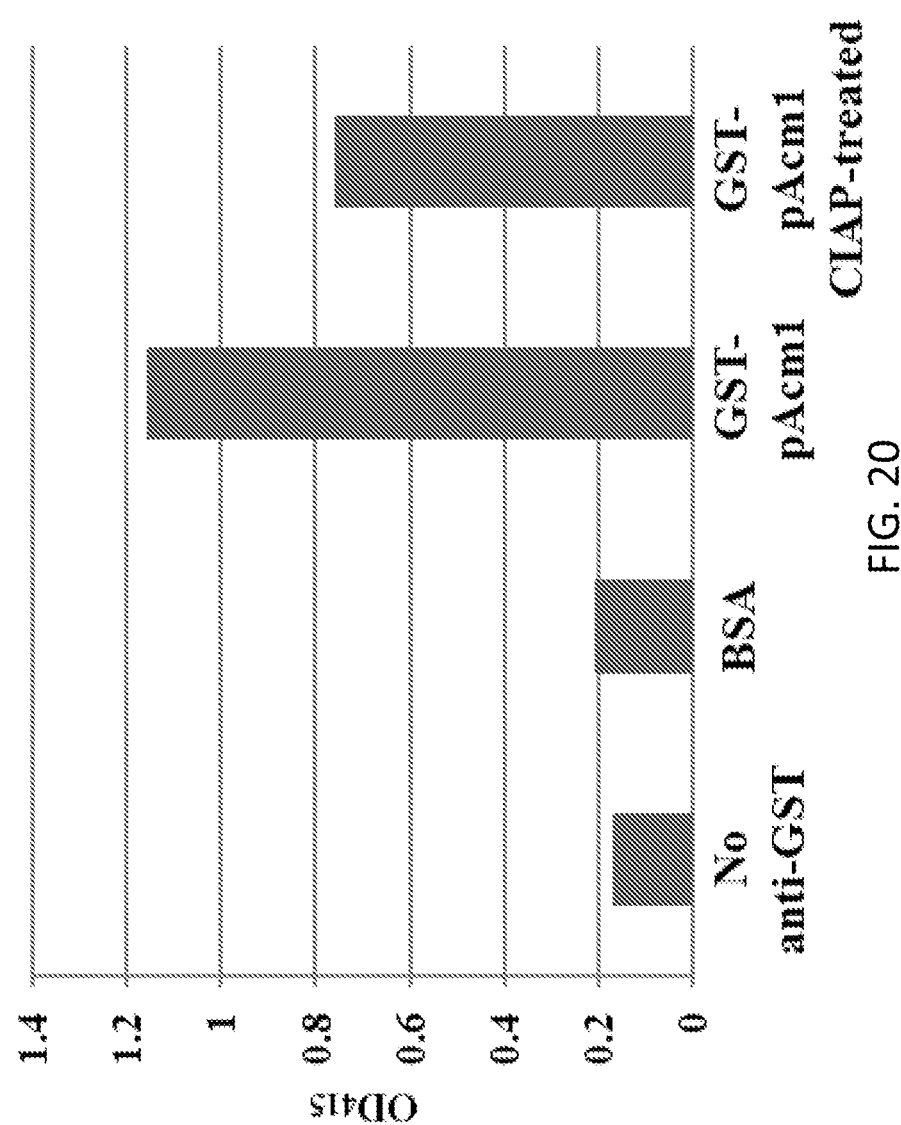
FIG. 20. Graph showing the results of pIMAGO based detection of Acm1 phosphorylation using sandwich ELISA assay.

As demonstrated by the data in FIG. 20, when anti-GST antibody was immobilized on a 96-well plate and then incubated with phosphorylated GST-tagged Acm1 yeast protein the resulting signal was much stronger than in the wells where anti-GST was omitted or unphosphorylated BSA was used instead of GST-pAcm1. Finally, a decrease in signal was observed after partial dephosphorylation of phospho-Acm1 by a general alkaline phosphatase (CIAP). These results demonstrate the ability of pIMAGO to selectively detect the phosphorylation signal of a phosphoprotein coupled to its antibody, thus offering a great opportunity for effective analysis of protein phosphorylation ensuing from a complex sample mixture.

13. Mass Spectrometry Analysis of Samples Enriched in Phosphorylated Polypeptides.

Figure 21A:
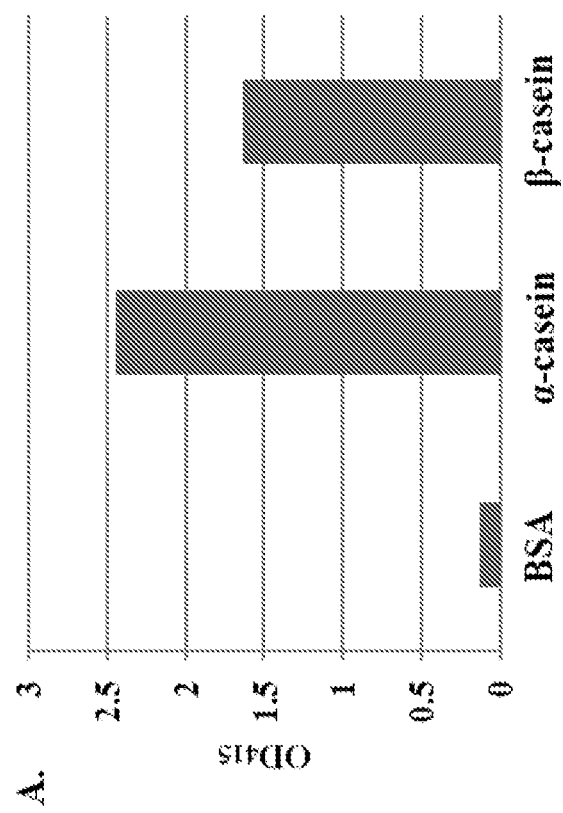
FIG. 21A. Graph showing the optical signal from BSA, α-casein or β-casein probed with pIMAGO.
Figure 21B:
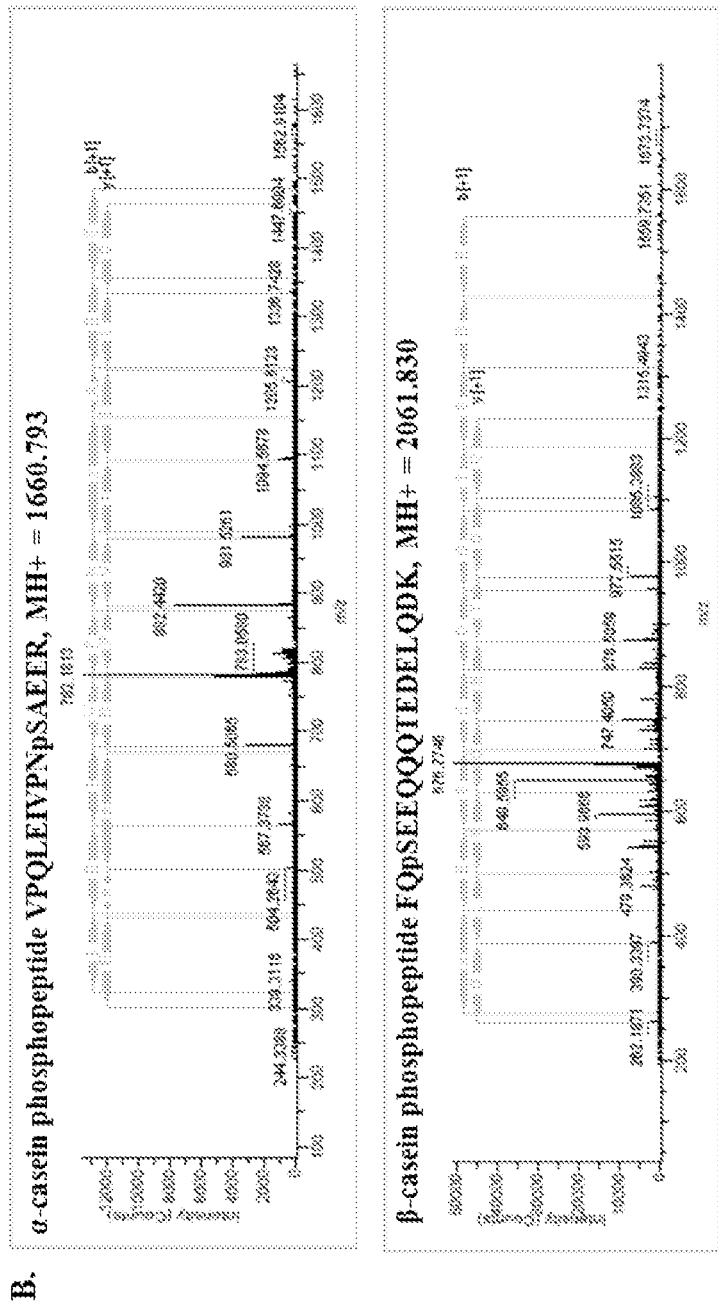
FIG. 21B. Sequence of polypeptides determined by mass spectrometry analysis of pIMAGO-labeled fragments of α-casein (upper panel) or β-casein (lower panel).

The ability of pIMAGO to detect protein phosphorylation and subsequently enrich its phosphopeptides after a digestion was also tested. Referring now to FIG. 21A; phosphorylated bovine α-casein and β-casein, available from Sigma-Aldrich, were immobilized on a plate and detected using a pIMAGO reagent based procedure. Following the tryptic digestion of the immobilized proteins, the resulting phosphopeptides were enriched using the same pIMAGO reagent and the whole complex captured using high-capacity streptavidin beads. Finally, the phosphopeptides were eluted and analyzed by LC-MS/MS. Referring now to FIG. 21B, the results provided in this figure show that only phosphorylated peptides were identified by mass spectrometry (MS/MS spectra for the two phosphopeptides are shown in FIG. 21B). These data demonstrate that pIMAGO based reagents and assays are useful tools for detecting phosphoproteins, enriching for them or their phosphopeptides, and thereby allowing for simultaneous quantitation of a protein's phosphorylation state and locating its phosphorylation sites.

Coupling pIMAGO-based detection and enrichment procedures with mass spectrometry is very useful for both the qualitative and quantitative assessment of protein phosphorylation. It provides a ready method for determining phosphorylation events, quantitation of any changes due to variation of experimental conditions, and identification of the modified sites, thus allowing the examination of a complete profile of a phosphoprotein.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

The invention claimed is:

1. A reagent for the detection of phosphorylated molecules, the reagent comprising:
 a linking core comprising at least one core selected from the group consisting of: a nanopolymer, a dendrimer molecule, and a core including an amide moiety;
 at least one moiety that includes a metal that is directly coupled to the linking core, the metal selected from the group consisting of: Ti(IV), Zr(IV), Fe(III), Ga(IV), Al(III), Sn(IV), Cu(II), and Zn(II); and
 at least one reporter group that is coupled to the linking core, the reporter group being selected from the group consisting of: biotin, an antibody, a lectin, a thiol, a fluorescent group, a chromophore, a chemiluminescent group and a radioactive group;
 wherein the metal and the at least one reporter group are associated with each other via the linking core and the moieties that include the metal bind to phosphorylated molecules.

2. The reagent of claim 1 wherein the linking core is selected from the group consisting of lysine and di(lysine).

3. The reagent of claim 1 wherein the linking core is selected from the group consisting of a nanopolymer, a dendrimer molecule, and a poly(lysine).

4. The reagent of claim 1 wherein the linking core comprises a dendrimer having at least 8 surface groups.

5. The reagent of claim 1 wherein the linking core comprises a dendrimer molecule having from about 8 surface groups to about 128 surface groups, the at least one moieties that include the metal are selected from at least one of a titania group and a zirconia group, and the sum of the number of reporter groups and number of moieties that include the metal is from 2 to about 128.

6. The reagent of claim 1 wherein the at least reporter group comprises from about 1 to about 40 reporter groups and the at least one moiety that includes the metal comprises from about 1 to about 30 moieties that include the metal, the moieties that include the metal selected from at least one of titania groups and zirconia groups.

7. The reagent of claim 1 further comprising at least one handle group selected from the group consisting of alkyne, azide, hydrazide, aldehyde, iodoacetyl, thiol, maleimide, and thiol.

8. A method for the detection of phosphorylated molecules in a sample comprising the steps of:
 contacting a reagent with a sample selected from the group consisting: of cells, tissue, proteins, lipids, or combinations thereof; said reagent comprising: a linking core comprising at least one selected from the group consisting of a nanopolymer, a dendrimer molecule, and a core including an amide moiety; a plurality of moieties that include a metal that is directly coupled to the linking core, the metal being selected from the group consisting of: Ti(IV), Zr(IV), Fe(III), Ga(IV), Al(III), Sn(IV), Cu(II), and Zn(II); and at least one reporter group that is coupled to the linking core, the reporter group being selected from the group consisting of: biotin, an antibody, a lectin, a thiol, a fluorescent group, a chromophore, a chemiluminescent group, and a radioactive group; wherein the metal and the at least one reporter group are associated with each other via the linking core and the moiety that include the metal binds to phosphorylated molecules, such that at least a portion of said reagent binds to a portion of the sample;
 removing at least a portion of any unbound reagent; and
 detecting the phosphorylated molecules in the sample by detecting the reporter groups of the reagent.

9. The method of claim 8 further comprising at least one procedure selected from the group consisting of: Western blotting, fluorescent imaging, chemilluminescence detection, spectrophotometric detection, high-through-put screening; mass spectrometric analysis, in-gel staining, in vitro kinase assays, and in vivo phosphorylation analysis.

10. The method of claim 8 wherein the linking core is selected from the group consisting of lysine and di(lysine).

11. The method of claim 8 wherein the linking core is selected from the group consisting of a nanopolymer, a dendrimer molecule, and a poly(lysine).

12. The method of claim 8 wherein the linking core comprises a dendrimer having at least 8 surface groups.

13. The method of claim 8, wherein the reagent further comprises at least one handle group selected from the group consisting of alkyne, azide, hydrazide, aldehyde, iodoacetyl, thiol, maleimide, and thiol.

14. The method of claim 13, wherein said detecting step is performed in a gel and the method further comprising the steps of:

extracting the phosphorylated molecules from the gel;
isolating the phosphorylated molecules using the at least one handle group; and
identifying the isolated phosphorylated molecules.

15. The method of claim 14, wherein said identifying step comprises performing mass spectrometric analysis on the isolated phosphorylated molecules.

16. A kit for the detection of phosphorylated molecules in a sample comprising a reagent said reagent comprising:
a linking core comprising at least one selected from the group consisting of a nanopolymer, a dendrimer molecule, and a core including an amide moiety; a plurality of moieties that include a metal that is directly coupled to the linking core, the metal being selected from the group consisting of: Ti(IV), Zr(IV), Fe(III), Ga(IV), Al(III), Sn(IV), Cu(II), and Zn(II); and at least one reporter group that is coupled to the linking core, the reporter group being selected from the group consisting of: biotin, an antibody, a lectin, a thiol, a fluorescent group, a chromophore, a chemiluminescent group and a radioactive group; wherein the metal and the at least one reporter group are associated with each other via the linking core and the moiety that include the metal bind to phosphorylated molecules.

17. The kit of claim 16 wherein the linking core is selected from the group consisting of lysine and di(lysine).

18. The kit of claim 16 wherein the linking core is selected from the group consisting of a nanopolymer, a dendrimer molecule, and a poly(lysine).

19. The kit of claim 16 wherein the dendrimer comprises at least 8 surface groups.

20. The kit of claim 16, wherein the reagent further comprises at least one handle group selected from the group consisting of alkyne, azide, hydrazide, aldehyde, iodoacetyl, thiol, maleimide, and thiol.

* * * * *